United States Patent [19]
Bonne et al.

[11] Patent Number: 6,019,505
[45] Date of Patent: Feb. 1, 2000

[54] TIME LAG APPROACH FOR MEASURING THERMAL CONDUCTIVITY AND SPECIFIC HEAT

[75] Inventors: Ulrich Bonne, Hopkins; David Kubisiak, Chanhassen; Robert J. Matthys, St. Anthony; Spencer B. Schuldt, Bloomington, all of Minn.

[73] Assignee: Honeywell Inc., Minneapolis, Minn.

[21] Appl. No.: 09/001,530

[22] Filed: Dec. 31, 1997

[51] Int. Cl.[7] .......................... G01K 17/06; G01K 17/08; G01N 25/18; G06F 15/20
[52] U.S. Cl. .......................... 374/40; 374/44; 73/204.17; 73/204.18; 364/557
[58] Field of Search ............................ 374/40, 43, 44; 73/204.16, 204.17, 204.18; 365/556, 557

[56] References Cited

U.S. PATENT DOCUMENTS

| | | | |
|---|---|---|---|
| 3,015,232 | 1/1962 | Schnoll | 73/204 |
| 3,335,606 | 8/1967 | Scarpa | 73/204 |
| 4,279,147 | 7/1981 | Djorup | 73/189 |
| 4,576,050 | 3/1986 | Lambert | 73/861.05 |
| 4,682,503 | 7/1987 | Higashi et al. | 73/755 |
| 4,713,970 | 12/1987 | Lambert | 73/861.05 |
| 4,944,035 | 7/1990 | Aagardl et al. | 364/556 |
| 4,961,348 | 10/1990 | Bonne | 73/861.02 |
| 5,031,126 | 7/1991 | McCulloch et al. . | |
| 5,150,611 | 9/1992 | Kleinhans | 73/204.14 |
| 5,184,509 | 2/1993 | Kienzle et al. | 73/204.14 |
| 5,193,388 | 3/1993 | Kleinhans | 73/204.14 |
| 5,237,523 | 8/1993 | Bonne et al. | 364/571.03 |
| 5,247,156 | 9/1993 | Favre | 219/209 |
| 5,303,167 | 4/1994 | Bonne | 364/556 |

FOREIGN PATENT DOCUMENTS

| | | |
|---|---|---|
| 0419873A | 4/1991 | European Pat. Off. . |
| 9206369A | 4/1992 | WIPO . |

OTHER PUBLICATIONS

Bonne et al., "Burstproof, Thermal Pressure Sensor for Gases", 1994 Solid State Sensor and Actuator Workshop, 2 pages.

Lambert et al., "An air flow sensor based on interface thermal wave propagation", *J. Appl. Phys.*, 59(1), Jan. 1986, 3 pages.

Bonne et al., "Natural Gas Flow and Property Sensor", *GRI Engine Technology Advisory Committee Meeting*, May 1996, 5 pages.

Healy et al., "The Theory of the Transient Hot–Wire Method for Measuring Thermal Conductivity", *Physics*, 82C (1976) pp. 392–408.

Protodyanakonow et al., "The Use of Probes in Investigating Two–Phase Flow", *Fluid Mech., Soviet Res.*, 12, No. 3, (May– Jun. 1983), pp. 98–157.

Carslaw et al., "Conduction of Heat in Solids", $2^{nd}$ Edition, Clarendon Press, Oxford, UK (1959), 7 pages.

Mylroi, "Cross–Correlation Flow Measurement Systems", *G.B.*, 12, No. 6–7, 1977, 4 pages.

Kubisiak et al, "Microamemometer–Based Gas Flow Sensing", *IGT Symposium of Natural Gas Quality Measurement*, Jul. 1990, 18 pages.

*Primary Examiner*—Vit Miska
*Attorney, Agent, or Firm*—Ian D. Mackinnon

[57] ABSTRACT

A method and apparatus for providing a more direct approach to determine the thermal conductivity, thermal diffusivity and specific heat of a fluid of interest, independently of the amplitude of the sensor output. This is preferably accomplished by measuring one or more variable phase or time lags between selected input and output AC signals, and directly deriving the thermal conductivity, thermal diffusivity and specific heat therefrom. Such derivation is therefore less dependent than amplitude-based sensors on occasional or unpredictable drift in sensor resistive elements.

17 Claims, 15 Drawing Sheets

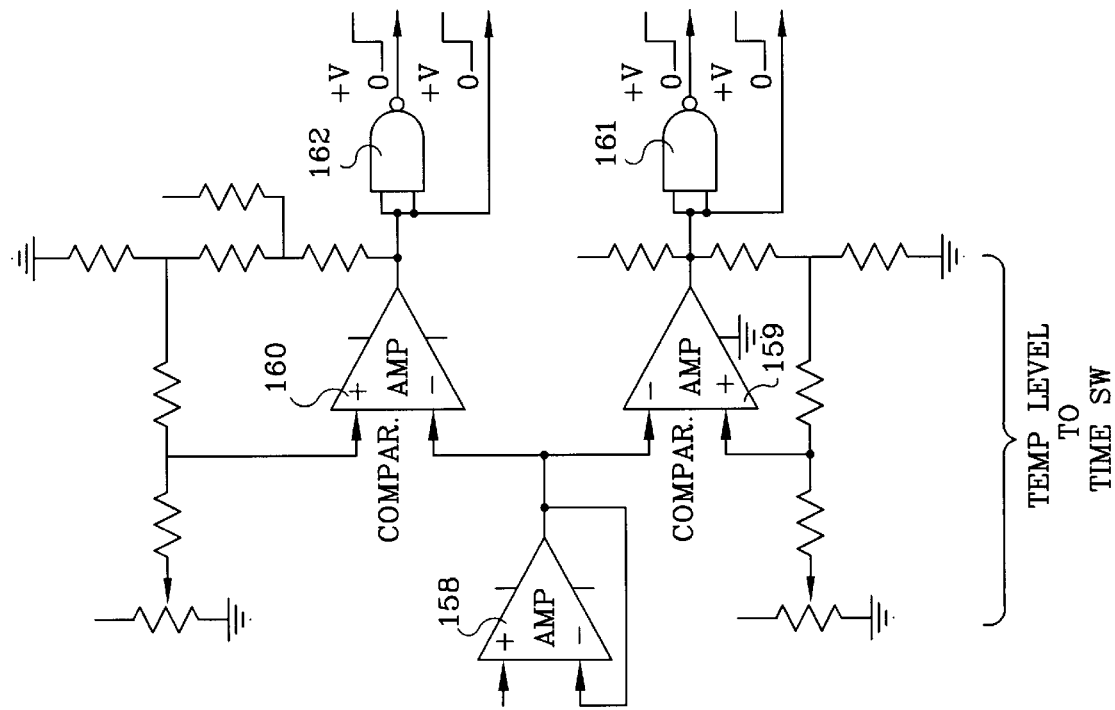
Fig. 5B
(PRIOR ART)
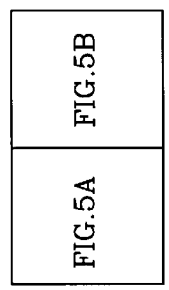

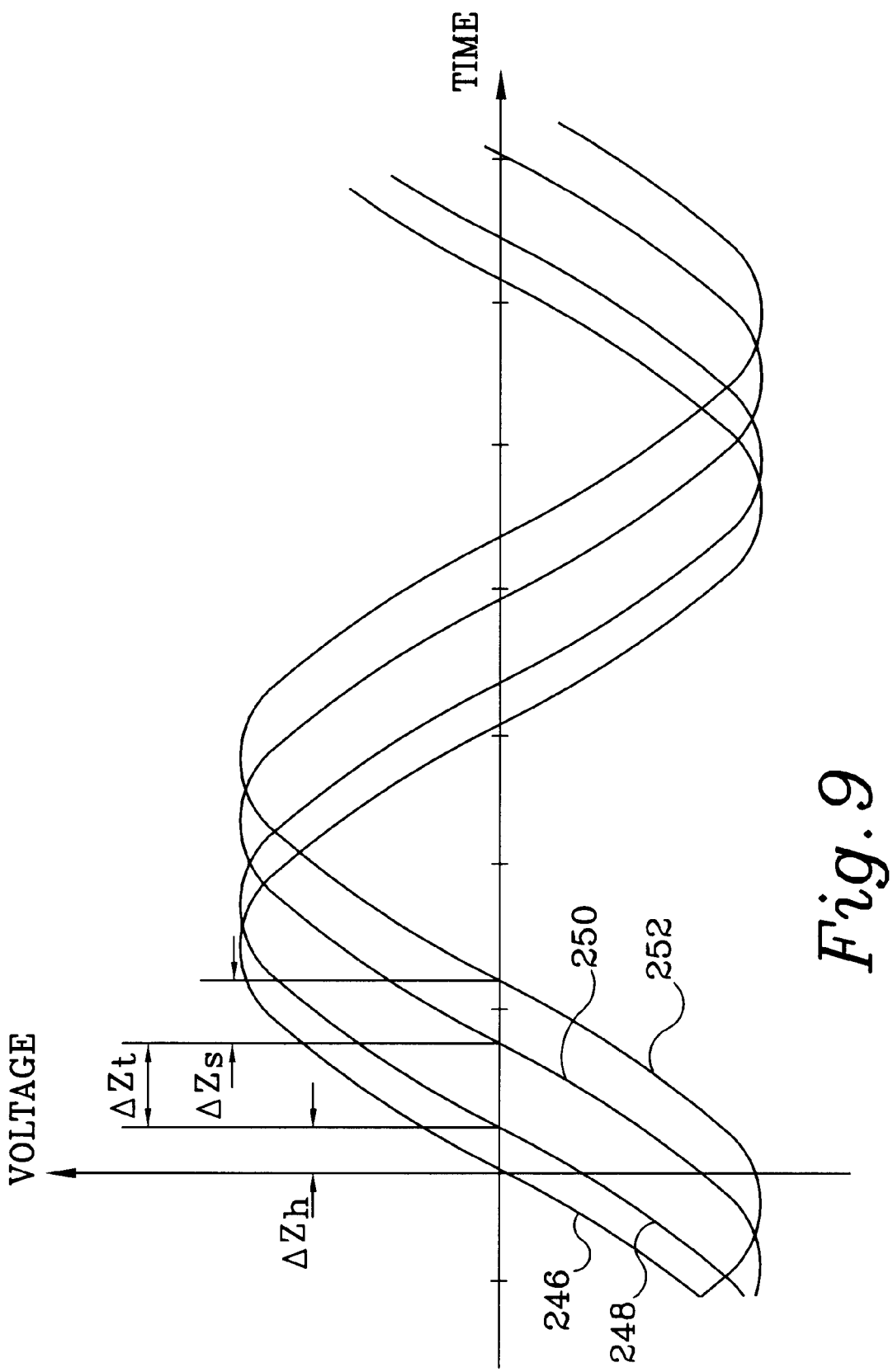

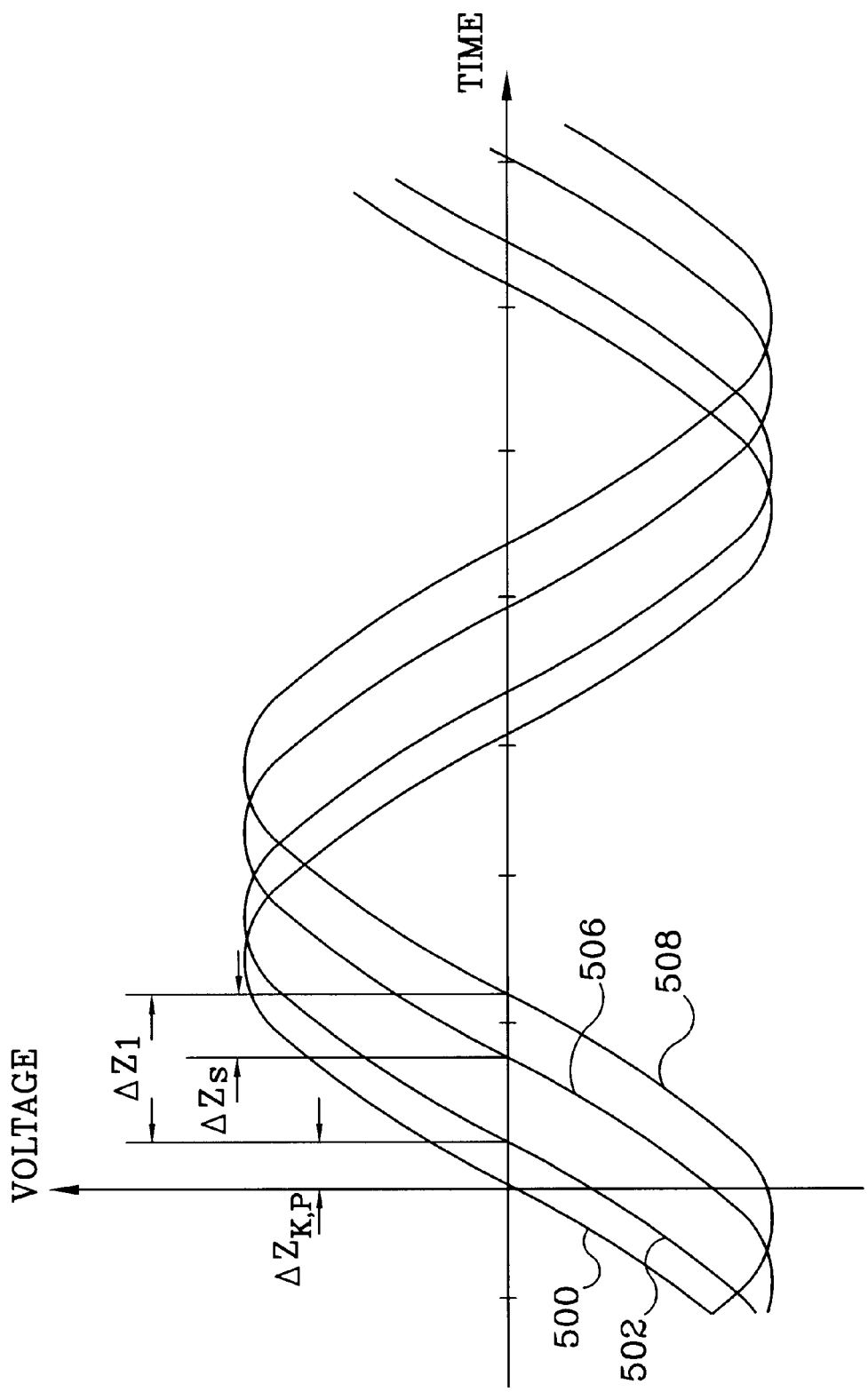

TIME LAG APPROACH FOR MEASURING THERMAL CONDUCTIVITY AND SPECIFIC HEAT

CROSS REFERENCE TO APPLICATIONS

The present application is related to U.S. patent application Ser. No. 09/002/56, filed Dec. 31, 1997, entitled "METHOD AND APPARATUS FOR MEASURING SELECTED PROPERTIES OF A FLUID OF INTEREST USING A SINGLE HEATER ELEMENT", U.S. patent application Ser. No. 09/002/57, filed Dec. 31, 1997, entitled "TIME LAG APPROACH FOR MEASURING FLUID VELOCITY", U.S. patent application Ser. No. 09/00/735, filed Dec. 31, 1997, entitled "SELF-OSCILLATING FLUID SENSOR", and U.S. patent application Ser. No. 09/00/453, filed Dec. 31, 1997, entitled "DIGITAL SENSOR WITH FFT", which are all assigned to the assignee of the present invention and incorporated herein by reference.

BACKGROUND OF THE INVENTION

1. Field of the Invention

The present invention relates to the measurement of certain physical properties of fluids and, more particularly, to the determination of the thermal conductivity and specific heat of fluids.

2. Description of the Prior Art

A number of approaches have been devised to measure the thermal conductivity, thermal diffusivity and specific heat of a fluid of interest. A traditional approach to determining thermal diffusivity, $D_t$, and specific heat, $c_p$, has been via calorimetry using reversible step increases of energy fed to a thermally isolated or adiabatic system. Such devices are bulky, slow and cumbersome.

Approaches for determining the thermal conductivity, k, of fluids typically use various types of detectors including resistive bridge type sensors. One such approach is described in U.S. Pat. No. 4,735,082 in which thermal conductivity is detected using a Wheatstone bridge in which a filament in one leg of the bridge is placed or positioned in a cavity through which the sample gas of interest is passed. The filament is used to introduce a series of amounts of thermal energy into the fluid of interest at various levels by varying the input voltage which, are, in turn, detected at another leg as voltage difference signals. Integration of the changes of the value of the successive stream of signals yields a signal indicative of the heat dissipation through the fluid, and thus, the thermal conductivity of the fluid.

Further to the measurement of thermally induced changes in electrical resistance, as will be discussed in greater detail below, especially with reference to prior art FIGS. 1–5, very small and very accurate "microbridge" semiconductor chip sensors have been described in which etched semiconductor "microbridges" are used as heaters and sensors. Such sensors might include, for example, a pair of thin film sensors around a thin film heater for measuring flow rates. Semiconductor chip sensors of the class described are treated in a more detailed manner in one or more of patents such as U.S. Pat. Nos. 4,478,076, 4,478,077, 4,501,144, 4,651,564, and 4,683,159, all of common assignee with the present invention.

An improvement for measuring the thermal conductivity, thermal diffusivity and specific heat of a fluid is disclosed in U.S. Pat. No. 4,944,035 to Aagard et al. Aagard et al. discloses using a microbridge structure that has a heater film and at least one spaced sensor films. A pulse of electrical energy is applied to the heater at a level and duration such that both a transient change and a substantially steady-state temperature occur in the sensor. The thermal conductivity of the fluid of interest is determined based upon a known relation between the sensor output and the thermal conductivity at steady-state sensor temperatures. The specific heat and thermal diffusivity of the fluid of interest are determined based on a known relation among the thermal conductivity, the rate of change of the sensor output during a transient temperature change in the sensor, and the thermal diffusivity and specific heat.

A limitation of the Aagard et al. approach is that the relation among the thermal conductivity, the rate of change of the sensor output during a transient temperature change in the sensor, and the thermal diffusivity and specific heat must be previously determined and stored in a data bank. The measured rate of change at the sensor output must then be correlated to the desired specific heat value using the previously determined relation. This may require a significant amount of support hardware and/or software.

Another limitation of Aagard et al. is that the derived specific heat value is dependent on the rate of change of the sensor output between two reference temperatures. That is, the rate of change of the sensor output may depend on the amplitude of the sensor output signal, and thus the resistance of the sensor. It is known that the resistance of many materials vary with time, at least to some degree, thus adding an additional potential error source. It would be desirable, therefore, to provide a more direct approach to determine the thermal conductivity, thermal diffusivity and specific heat of a fluid of interest, independently of the amplitude of the sensor output.

SUMMARY OF THE INVENTION

The present invention overcomes many of the disadvantages associated with the prior art by providing a more direct approach to determine the thermal conductivity, thermal diffusivity and specific heat of a fluid of interest, independently of the amplitude of the sensor output. This is preferably accomplished by measuring one or more variable phase or time lags between selected input and output signals, as more fully described below, and directly deriving the thermal conductivity, thermal diffusivity and specific heat therefrom. Because time-lag measurements may be made at, for example, zero crossing points of the selected signals, the derived thermal conductivity, thermal diffusivity and specific heat values may be independent of the amplitude of the sensor output.

Generally, the present invention includes a heater element and a spaced sensor element, both of which are disposed in and closely coupled to a fluid medium (fluid or gas) of interest at substantially zero flow. A time-varying input signal is provided to the heater element, which heats the surrounding fluid. Of interest is the transit time for the temperature disturbance to travel from the heater element to the sensor element. The thermal diffusivity and specific heat of the fluid of interest can be calculated from this transit time value.

One approach to measuring the transit time between the heater element and sensor element is to start a timer when the heater input signal crosses a predetermined threshold, and stop the timer when the temperature response of the sensor element crosses a predetermined threshold. While such an approach may be sufficient for many applications, several factors should be considered for higher precision applications.

A first factor is the non-zero heater time lag between the input signal to the heater element and the elevated temperature response of the heater element (and thus fluid). The heater time lag is typically dominated by the thermal conductivity, k, of the fluid of interest, at least for microbridge structures as contemplated by a preferred embodiment of the present invention. As discussed in U.S. patent application Ser. No. 09/002/56, entitled "METHOD AND APPARATUS FOR MEASURING SELECTED PROPERTIES OF A FLUID OF INTEREST USING A SINGLE HEATER ELEMENT", the thermal conductivity, k, of the fluid of interest can be derived from the heater time lag.

A second factor is a non-zero sensor time lag between the arrival of the temperature disturbance at the sensor element and the resistance change in the sensor element. That is, the temperature of the sensor element typically does not react instantaneously to a temperature change in the fluid, primarily due to the sensors non-zero thermal mass.

One approach to reduce the effects of these factors is to measure the heater and sensor time lags during a calibration procedure. This can be accomplished by providing a heater input signal to the heater element, and a sensor input signal to the sensor element. The heater time lag and the sensor time lag can be determined by monitoring the transient temperature responses of the heater and sensor elements, respectively. To obtain a more accurate transit time for the temperature disturbance in the fluid, the heater time lag and the sensor time lag may then be subtracted from the time lag measured between the heater input signal and the resulting temperature response of the sensor element during operation.

Another approach is to provide heat to the sensor element via a sensor input signal during operation. The sensor input signal is preferably controlled to provide a frequency, phase and amplitude that produce a resulting temperature response in the sensor element that tracks the temperature disturbance in the fluid. When this condition is satisfied, substantially zero heat is transferred from the fluid to the sensor element.

The proper phase and amplitude of the sensor input signal can be determined during a calibration procedure. In a preferred embodiment, the sensor element is first subjected to a vacuum condition, and a sensor input signal is provided to the sensor element. Because no fluid surrounds the sensor element, substantially no heat is transferred from the sensor element to the fluid. A sensor time lag between the sensor input signal and the resulting temperature response of the sensor element is measured and stored. A power/resistance ratio of the sensor element is also measured and stored.

The sensor element is then subjected to a fluid of interest. During operation, the phase of the sensor input signal is adjusted so that the resulting sensor time lag equals the sensor time lag measured under vacuum conditions. Likewise, the amplitude of the sensor input signal is adjusted so that the resulting power/resistance ratio equals the power/resistance ratio measured under vacuum conditions.

Accordingly, the sensor input signal heats the sensor element in phase and with the proper amplitude to match the temperature disturbance in the fluid, and substantially no heat is transferred from the fluid to the sensor element. This may help reduce or eliminate the sensor time lag as a factor when determining the transit time of the temperature disturbance.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 9 is a timing diagram showing the desired transit time $\Delta z_t$, the heater lag time $\Delta z_h$, and the sensor lag time $\Delta z_s$;

FIG. 18 is a timing diagram showing the various time lags measured by the embodiment of FIG. 11.

DETAILED DESCRIPTION OF THE PREFERRED EMBODIMENTS

Figure 1:
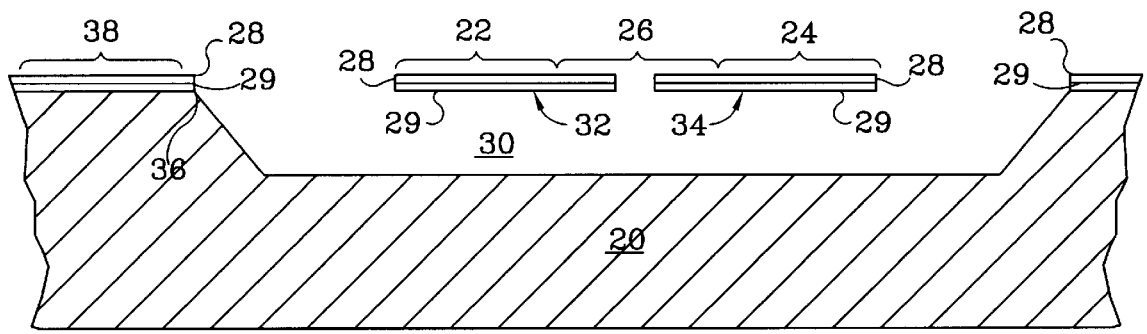
FIGS. 1, 2 and 3 are different views of a prior art embodiment of a microbridge flow sensor.

The present invention, then, is directed to a system which enables a more direct determination of selected fluid properties such as thermal conductivity, thermal diffusivity and specific heat, relatively independently of input and output signal amplitudes. The preferred embodiments of the approach contemplate disposing a microscopic sized heating element in a relatively static (zero flow) sample of the fluid of interest. The microsensor system or "microbridge", as it will be referred to herein, though not limiting, is presently preferred for several reasons. The system is extremely fast-reacting, is very accurate, very sensitive because of its advantageous coupling to the fluid of interest and small and adaptable to a variety of configurations.

The microbridge semiconductor chip sensor contemplated, for example, in certain embodiments preferred for the invention may resemble the form of one or more of the microbridge systems illustrated in the patents identified above. Such a system is exemplified by FIGS. 1–5 taken from U.S. Pat. No. 4,994,035 to Aagard et al. A discussion of that example will now be presented as it will be helpful in understanding the present invention. While the present discussion is believed sufficient, to the extent necessary, any additional material contained in the microbridge related patents cited is deemed to be incorporated herein by reference.

The prior art system of FIGS. 1–5 contemplates a pair of thin film temperature sensors 22 and 24, a thin film heater 26 and a support member 20 supporting the sensors and heater out of contact with the base substrate. Sensors 22 and 24 are disposed on opposite sides of heater 26. Support member 20 is a semiconductor, preferably silicon, chosen because of its adaptability to precision etching techniques and ease of electronic chip producibility. The embodiment includes two identical temperature sensing resistor grids 22 and 24 acting as the thin film heat sensors and a centrally located heater resistor grid 26 acting as the thin film heater.

Sensors 22 and 24 and heater 26 may be fabricated of any suitable, stable metal or alloy film. The metal used may be a nickel-iron alloy sometimes referred to as permalloy, with a composition of 80 percent nickel and 20 percent iron. The sensor and heater grids are encapsulated in a thin film of dielectric, typically comprising layers 28 and 29 and preferably silicon nitride, $Si_3N_4$ to form the film members.

Figure 2:
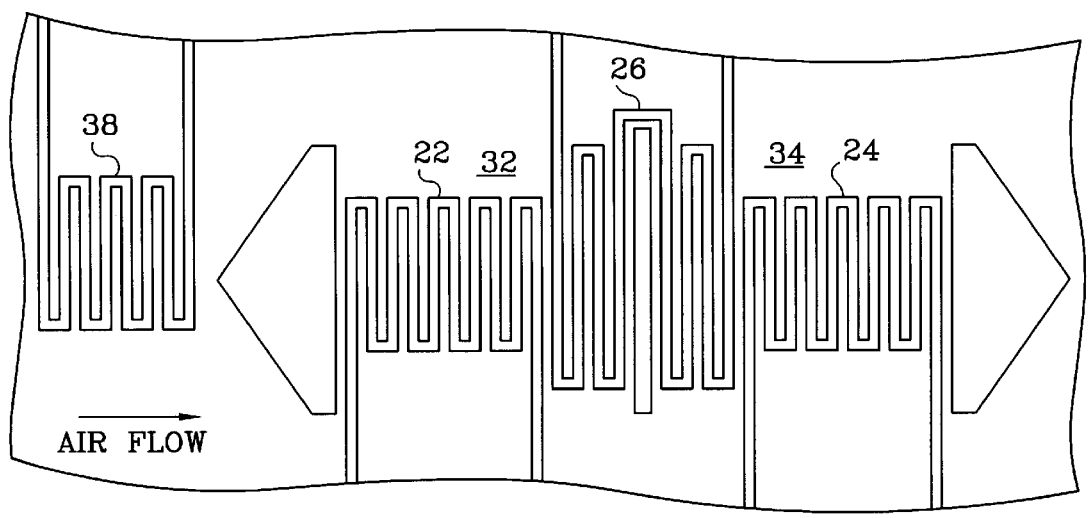

In the FIGS. 1 and 2, the sensor comprises two thin film members 32 and 34, with member 32 comprising sensor 22 and member 34 comprising sensor 24, each member comprising one-half of heater 26 and having a preferred dimension of 150 microns wide and 400 microns long.

The system further describes an accurately defined fluid space 30 that effectively surrounds elements 22, 24, 26, and is achieved by fabricating the structure on silicon surface 36. Thin film elements 22, 24 and 26 have thicknesses of approximately 0.08 to 0.12 micron with line widths on the order to 5 microns and spaces between lines on the order of 5 microns. The elements encapsulated in the silicon nitride film preferably have a total thickness of approximately 0.8 microns or less. The fluid space 30 may be fabricated by subsequently etching an accurately defined fluid space of about 100 microns deep into silicon body 20 beneath members 32 and 34.

Figure 3:
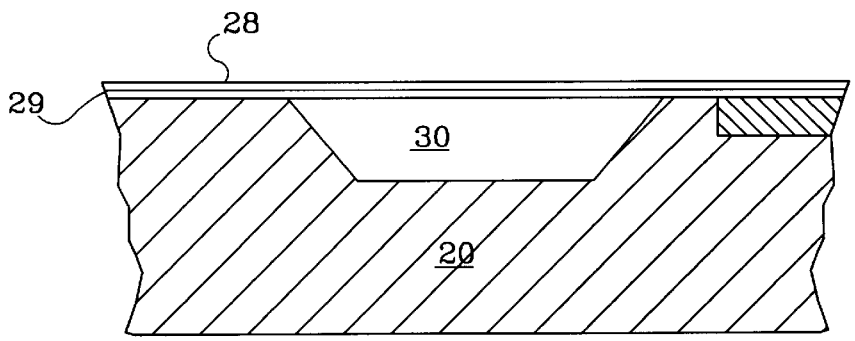

Members 32 and 34 connect to top surface 36 of semiconductor body 20 at one or more edges of depression or fluid space 30. As illustrated in FIG. 3, members 32 and 34 may be bridged across depression 30; alternately, for example, members 32 and 34 could be cantilevered over depression 30.

In the system shown, heat flows from the heater to the sensor by means of both solid and fluid couplings therebetween. Of note is the fact that silicon nitride ($Si_3N_4$), besides being a good electrical insulator, is also an effective solid thermal insulator. Because the connecting silicon nitride film within members 32 and 34 is a good insulator, heat transmission through the solid does not dominate the propagation of heat from heater 26. This further enhances the relative amount of the heat conducted to sensing resistors 22 and 24 from heater resistor 26 by flow through the surrounding fluid rather than through the supporting nitride film. Moreover, the supporting silicon nitride film has a low enough thermal conductivity that sensing resistor grids 22 and 24 can be located immediately adjacent or juxtaposed to heating resistor grid 26. Thus, sensing resistor grids 22 and 24 are in effect suspended rigidly in the fluid space proximate heater resistor 26 and act as thermal probes to measure the temperature of the air near and in the plane of heater resistor grid 26.

Figure 4:
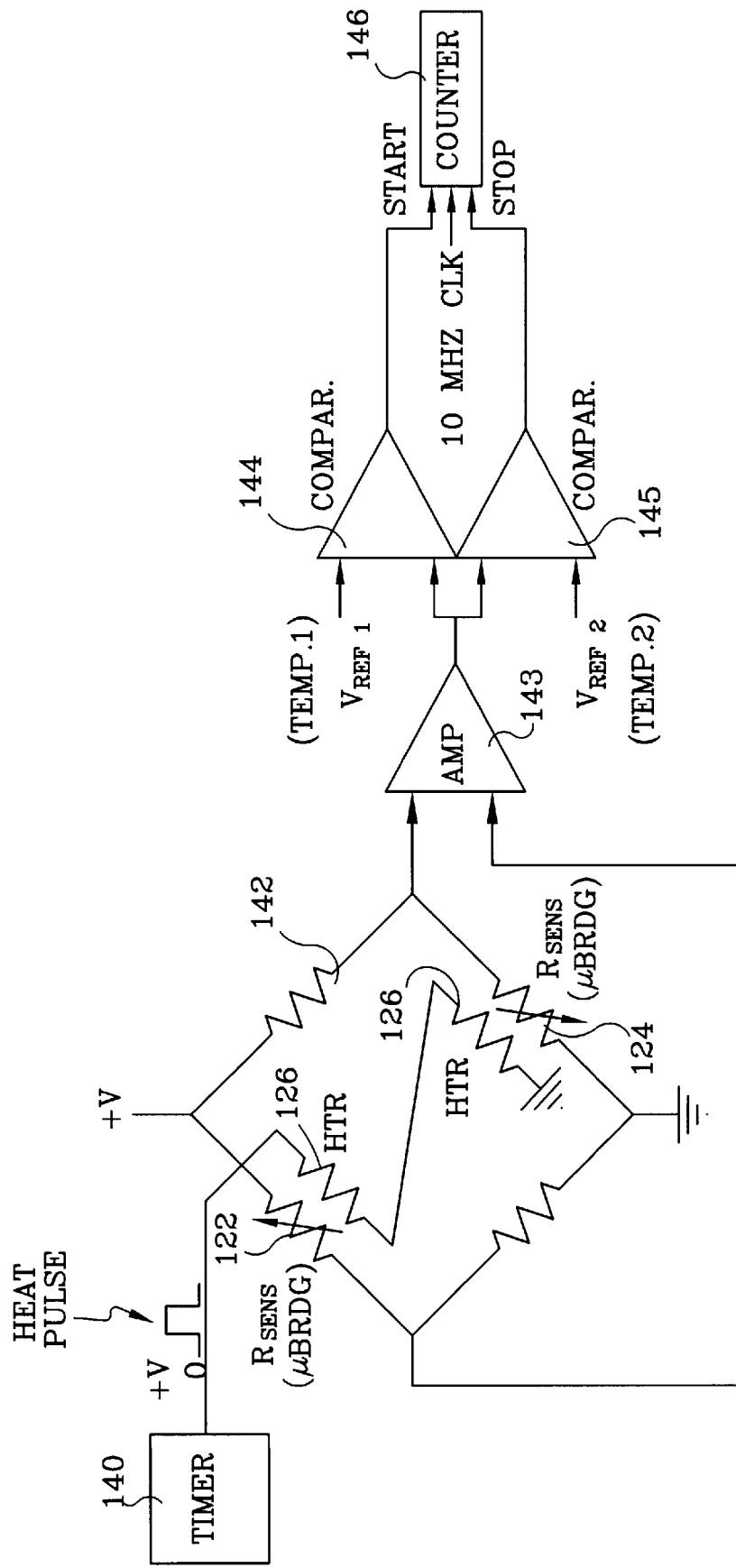
FIGS. 4 and 5 are typical circuits for use with the sensors of FIGS. 1–3 to determine the thermal conductivity, thermal diffusivity and specific heat of a fluid of interest.

The operation of the system in sensing thermal conductivity, thermal diffusivity and specific heat is described in detail in the above-referenced U.S. Pat. No. 4,994,035 to Aagard et al. Typical circuit implementation is discussed briefly with reference to FIGS. 4 and 5 to add some insight. FIG. 4 shows a pulse generator 140 providing square-wave electrical pulses to the heater 126. The heater couples the heat pulse to the sensors 122 and 124 in the bridge 142, primarily through the fluid. The output of the bridge is connected through an amplifier 143 to a pair of comparators 144 and 145 which operate "start" and "stop" inputs to a counter 146 which counts 10 MHz clock pulses. The counter measures the time interval between two reference temperatures $T_2$ and $T_1$ at sensors 122 and 124.

Figure 5A:
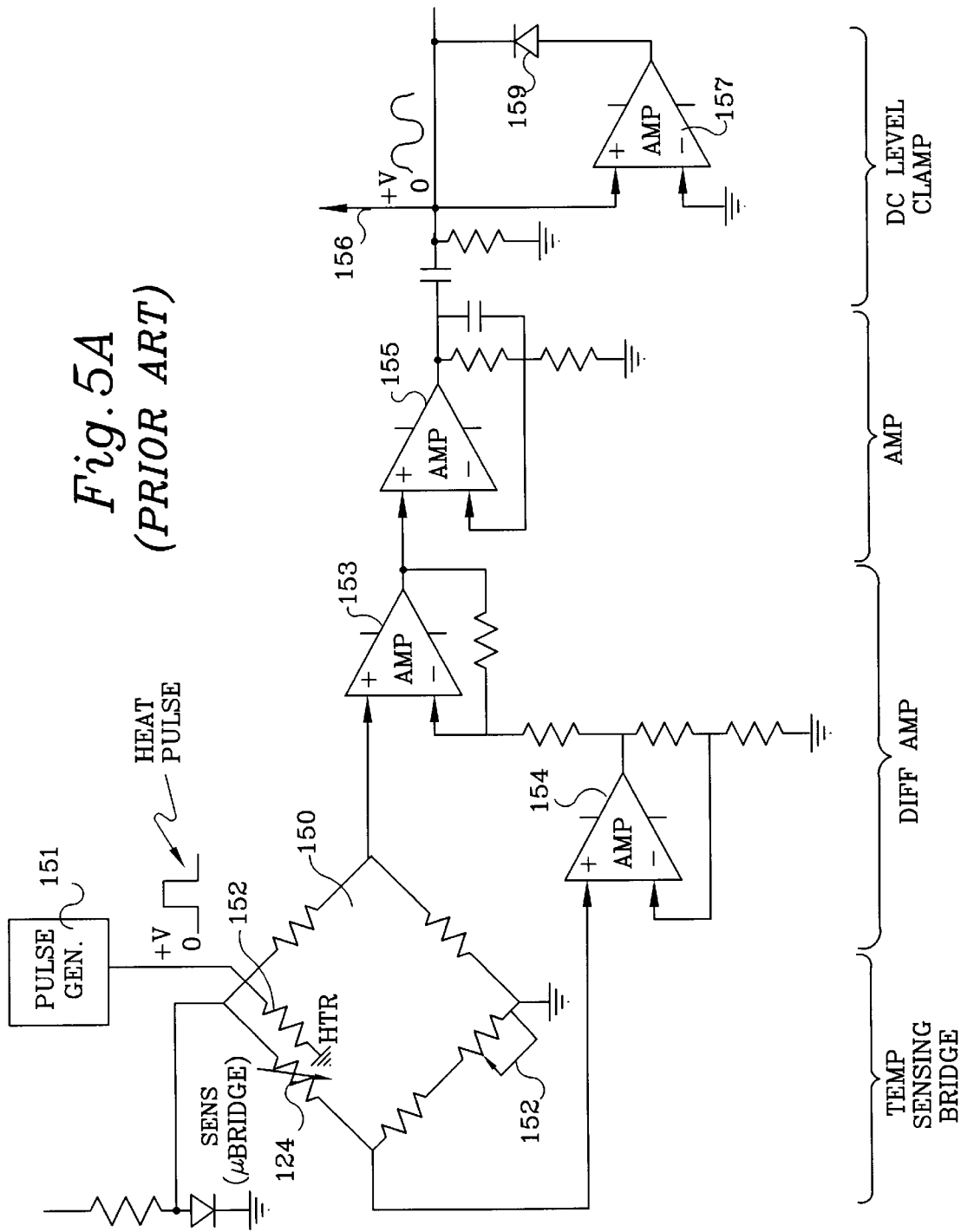

FIG. 5 is similar to FIG. 4, but provides more detail. The bridge configuration is a heater-space-sensor configuration. The sensor resistance arm of the microbridge is set into a Wheatstone bridge 150 at 124. Another proximate resistive arm 122 is fed a voltage pulse from pulse generator 151 to provide a heat pulse into a microbridge element 126. The Wheatstone bridge 150 also may contain a nulling balancing resistor 152 which can be used to initially zero the device. The microbridge resistor sensor 124 in the Wheatstone bridge receives the heat pulse from heater element 122 principally by thermal conduction through the surrounding fluid. Some conduction, of course, does occur through the solid microbridge substrate and surroundings.

The circuitry of FIG. 5 is conventional and can readily be explained with reference to its functional operation with regard to processing the bridge output signal. The voltage output signals of the bridge 150 are amplified by differential amplifiers 153 and 154 in a differential amplifier section. The balance signal is further amplified by a high gain amplifier at 155. The signal at 156 as is the case with the signal at 147 in FIG. 4 is in the form of a DC voltage signal, U, the amplitude of which is solely related to the thermal conductivity of the fluid of interest as discussed above.

The remainder of the circuitry of FIG. 5 includes a DC level clamping amplifier 157 and isolation amplifier 158. The temperature level, time-related switching and counting circuitry includes comparators 159 and 160 together with Nand gates 161 and 162 having outputs which are connected to the counter timing device (not shown) as in FIG. 4. The output signal from the Wheatstone bridge, U, represents the voltage imbalance caused by the temperature change in microbridge sensor or sensors induced by the corresponding heater pulse output. Because the magnitude of this imbalance is related directly to the amount of energy absorbed by the sensor or sensors, the amplitude of the signal is directly related to the thermal conductivity, k. Using previously derived calibration data, the thermal conductivity can thus determined.

By measuring the time needed for the sensor temperature to rise or fall between two or more known reference temperature values or markers as represented by sensor resistance or bridge voltage outputs, a measure related to the thermal diffusivity and specific heat of the fluid of interest is obtained. The timing device may be a conventional 10 MHz pulse counter or the like.

A limitation of this approach is that a relation among the thermal conductivity, the rate of change of the sensor output during a transient temperature change in the sensor, and the thermal diffusivity and specific heat must be previously determined and stored in a data bank. The measured rate of change at the sensor output must then be correlated to the desired specific heat value using the previously determined relation. This may require a significant amount of support hardware and/or software.

Another limitation is that the derived thermal diffusivity and specific heat values are dependent on the rate of change of the sensor output between two reference temperatures. That is, the rate of change of the sensor output may depend on the amplitude of the sensor output signal, and thus the resistance of the sensor. It is known that the resistance of many materials vary with time, at least to some degree, thus adding an additional potential error source.

Figure 6:
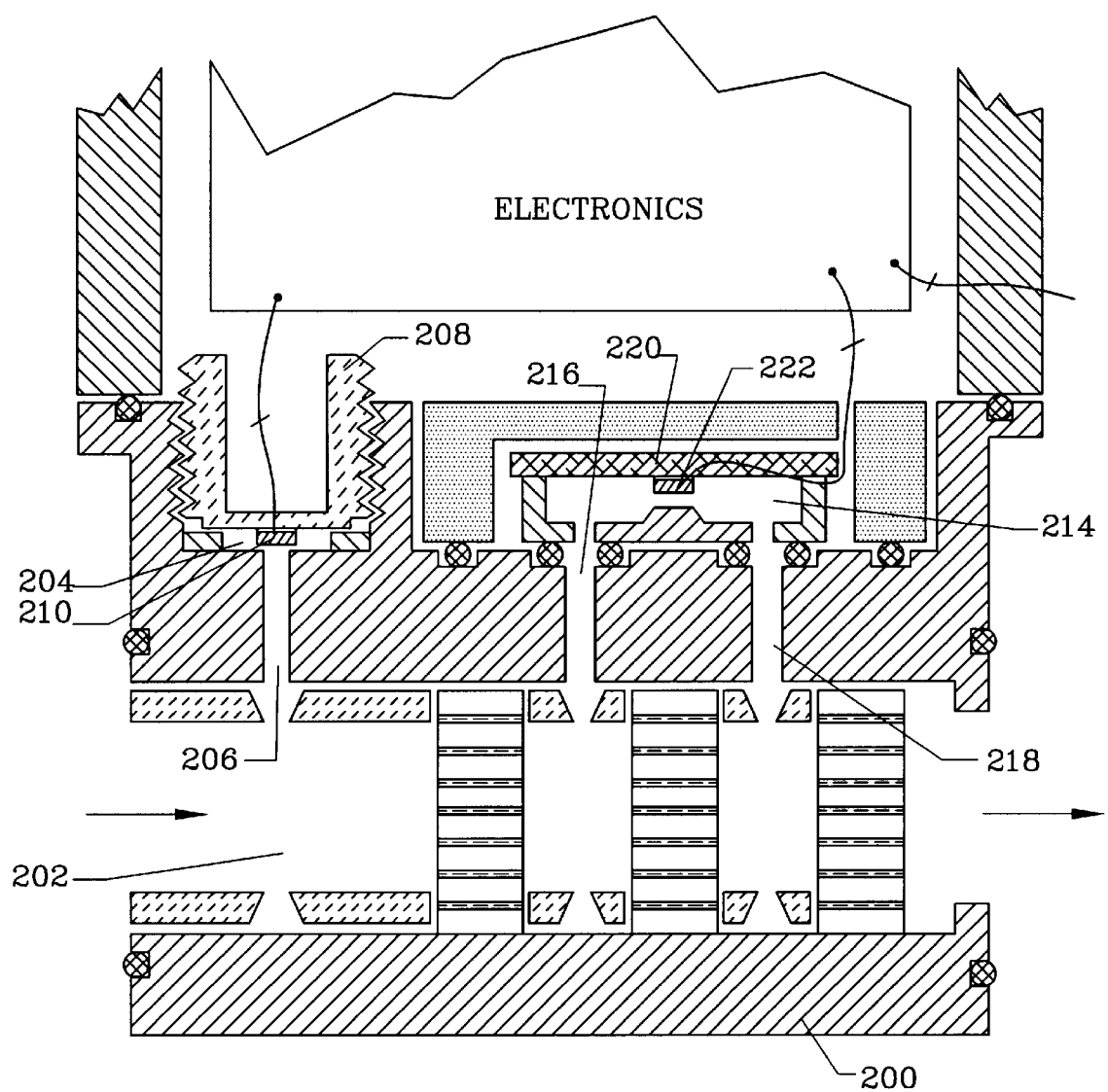
FIG. 6 is partial cut-away view of a microbridge sensor package.

FIG. 6 is partial cut-away view of a microbridge sensor package placed in line with a flow pipe. A main flow channel 200 having a central bore 202 is connected to the pipe that carries a fluid of interest. A first chamber 204 is in fluid communication with the central lumen 202 of the main flow channel 200 via a single bore 206. A header 208 having a first microbridge sensor 210 mounted thereto is inserted into the first chamber 204 and secured to the main flow channel 200 as shown. In this configuration, the first microbridge sensor is exposed to the fluid of interest with substantially zero flow. The first microbridge sensor 210 is typically used to measure fluid properties such as thermal conductivity, thermal diffusivity, specific heat, temperature and pressure.

A second sensor 222 is positioned in a small bypass channel 214. In this configuration, the second microbridge sensor is exposed to the flow of the fluid of interest. The second microbridge sensor 222 is typically used to measure fluid velocity.

Figure 7:
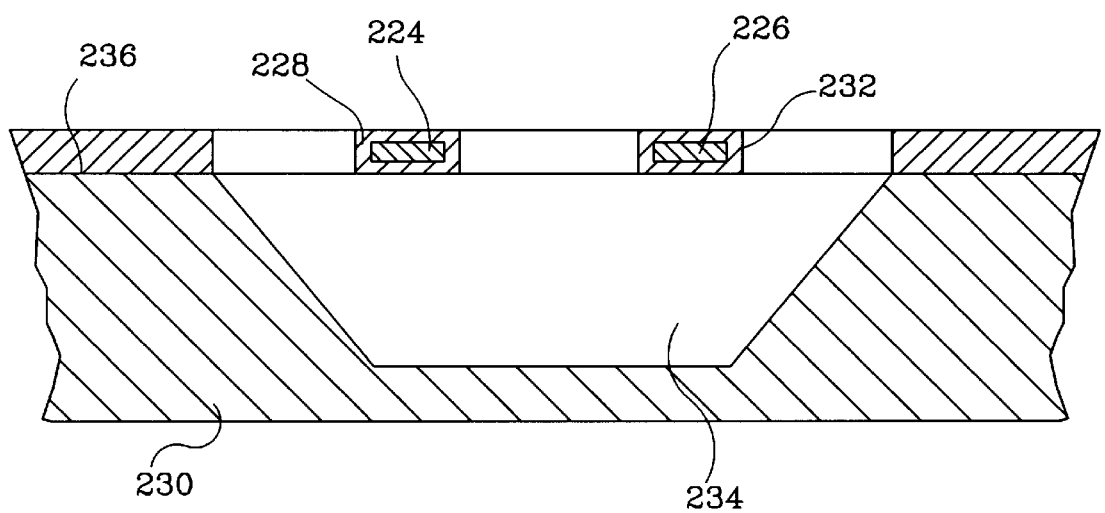
FIG. 7 is an illustrative cross sectional view of a microbridge in accordance with the present invention.

FIG. 7 is an illustrative cross sectional view of a microbridge system in accordance with the present invention. As indicated above, the present invention provides apparatus and methods for allowing accurate determination of selected fluid properties including thermal conductivity, thermal diffusivity, and specific heat in a more direct manner, independent of signal amplitudes.

Generally, the present invention includes a heater element 224 and a spaced sensor element 226, both of which are disposed in and closely coupled to a fluid medium (fluid or gas) of interest at substantially zero flow. A time-varying input signal is provided to the heater element 224, which heats the surrounding fluid. Of interest is the transit time for the temperature disturbance to travel from the heater element 224 to the sensor element 226. The thermal diffusivity and specific heat of the fluid of interest can be calculated from this transit time value.

The heater element 224 is shown having a support member 228 that supports the heater element 224 out of contact with the base substrate 230. Together, the heater element 224 and support member 228 form a heater film member. Likewise, the sensor element 226 is shown having a support member 232 that supports the sensor element 226 out of contact with the base substrate 230. Together, the sensor element 226 and support member 232 form a sensor film member.

Heater element 224 and sensor element 226 may be fabricated of any suitable, stable metal or alloy such as platinum, Nickel, Iron-Nickel, etc. Beater element 224 and sensor element 226 may be any resistive element including a wire, but are preferably a film. Moreover, heater element 224 and sensor element 226 may be of any shape including a grid pattern as described above, or simply a line. As indicated above, the heater element 224 and sensor element 226 are preferably encapsulated in a thin film of dielectric, such as silicon nitride, $Si_3N_4$, to form the support members 228 and 232.

An accurately defined fluid (air or liquid) space 234 is preferably provided which effectively surrounds heater element 224 and sensor element 226, and is achieved by fabricating the structure on silicon surface 236. Heater element 224 and sensor element 226 preferably have thicknesses of approximately 0.08 to 0.12 micron, with line widths on the order to 5 microns and, if a grid is used, spaces between lines on the order of 5 microns. The fluid space 234 may be fabricated by subsequently etching an accurately defined silicon-free space of about 100 microns deep into silicon substrate 236 beneath heater element 224 and sensor element 226.

Support member 228 and heater element 224 preferably connect to top surface 236 of semiconductor substrate 230 at one or more edges of etch-pit or depression 234. Support member 228 and heater element 224 may bridge across depression 234 as shown, or alternately, for example, cantilevered over depression 234. Likewise, support member 232 and sensor element 226 preferably connect to top surface 236 of semiconductor substrate 230 at one or more edges of depression or fluid space 234. Support member 232 and sensor element 226 may also bridge across depression 234 as shown, or alternately, for example, cantilevered over depression 234. It is recognized that any number of heater and sensor elements may be provided in a like manner. However, for illustration purposes, only one heater element 224 and one sensor element 226 are shown.

Figure 8:
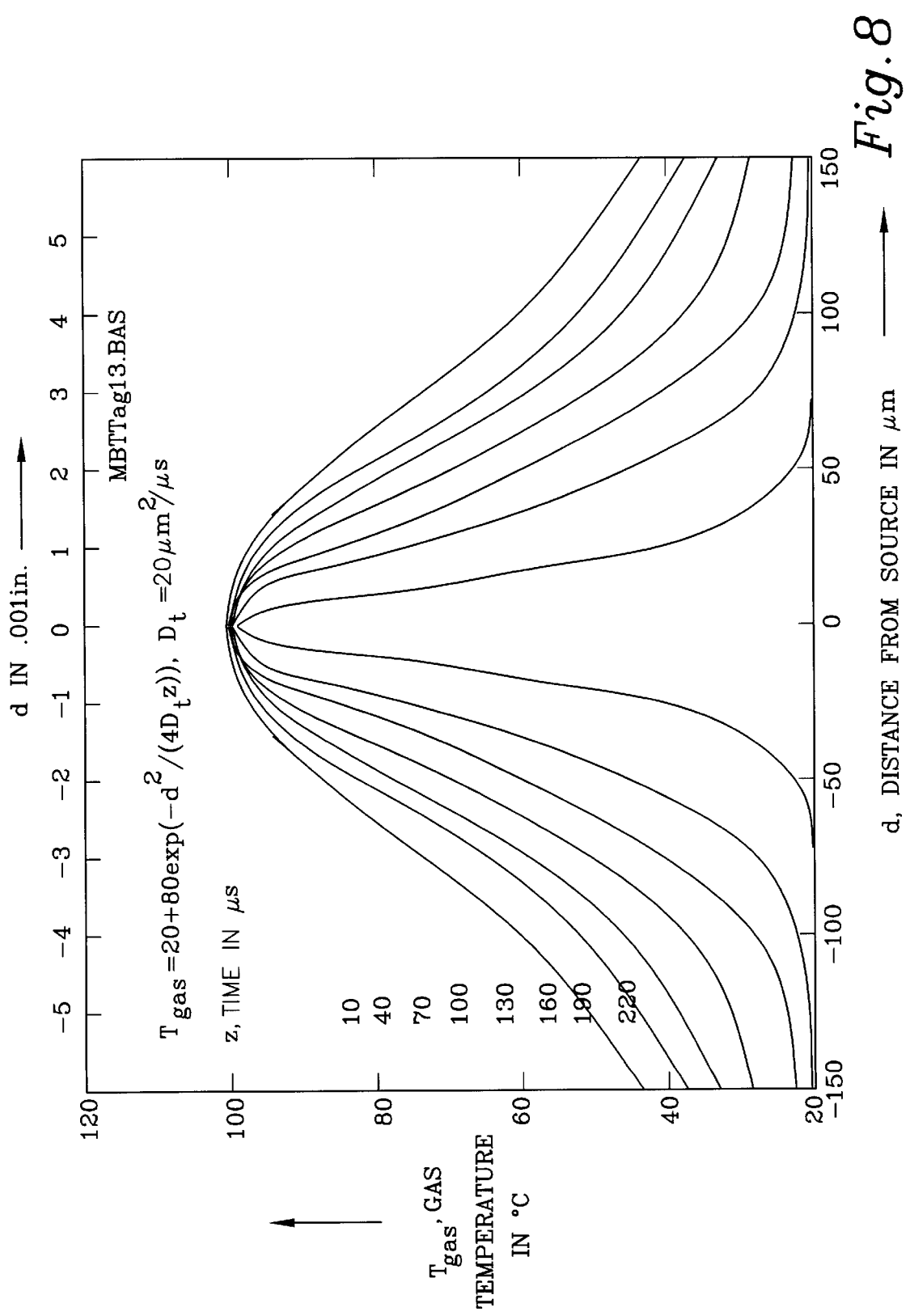
FIG. 8 is a graph showing a temperature disturbance produced by a heater element versus time.

FIG. 8 is a graph showing an illustrative temperature disturbance produced by a heater element versus time. As can be seen, the temperature disturbance does not propagate through the fluid at a uniform rate.

One approach to measuring the transit time of the temperature disturbance from the heater element to the sensor element is to start a timer when the heater input signal crosses a predetermined threshold, and stop the timer when the temperature response of the sensor element crosses a predetermined threshold. While such an approach may be sufficient for many applications, several factors should be considered for higher precision applications.

A first factor is the non-zero heater time lag $\Delta z_h$ (a.k.a $\Delta z_{k,p}$) between the heater input signal and the elevated temperature response of the heater element (and fluid). An illustrative heater input signal and elevated temperature response of the heater element are shown at 248 and 250 of FIG. 9, respectively. The heater time lag $\Delta z_h$ is typically dominated by the thermal conductivity, k, of the fluid of interest, at least for microbridge structures as contemplated by a preferred embodiment of the present invention. As discussed in U.S. patent application Ser. No. 09/002/56, entitled "METHOD AND APPARATUS FOR MEASURING SELECTED PROPERTIES OF A FLUID OF INTEREST USING A SINGLE HEATER ELEMENT", the thermal conductivity, k, of the fluid of interest can be derived from the heater time lag.

A second factor is the non-zero sensor time lag $\Delta z_s$ between the arrival of the temperature disturbance at the sensor element and the resistance change in the sensor element. That is, the temperature of the sensor element typically does not react instantaneously to a temperature change in the fluid, primarily because of the sensors non-zero thermal mass. This is explicitly shown in FIG. 9 wherein the arrival of the temperature disturbance at the sensor is shown at 250, and the resistive response of the sensor element is shown at 252.

One approach to reduce the effects of $\Delta z_h$ and $\Delta z_s$ is to measure the heater $\Delta z_h$ and sensor $\Delta z_s$ time lags during a calibration procedure. This can be accomplished by providing a heater input signal to the heater element, and a sensor input signal to the sensor element. The heater time lag $\Delta z_h$ and the sensor time lag $\Delta z_s$ can then be determined by monitoring the transient temperature responses of the heater and sensor elements, respectively. To obtain a more accurate transit time $\Delta z_t$ for the temperature disturbance in the fluid, the heater time lag $\Delta z_h$ and the sensor time lag $\Delta z_s$ may then be subtracted from the time lag measured between the heater input signal and the temperature response of the sensor element.

Another approach is to provide heat to the sensor element via a sensor input signal during operation. The sensor input signal is preferably controlled to provide a frequency, phase and amplitude that produce a resulting temperature response in the sensor element that tracks the temperature disturbance of the fluid. When this condition is satisfied, substantially zero heat is transferred from the fluid to the sensor element.

Figure 10A:
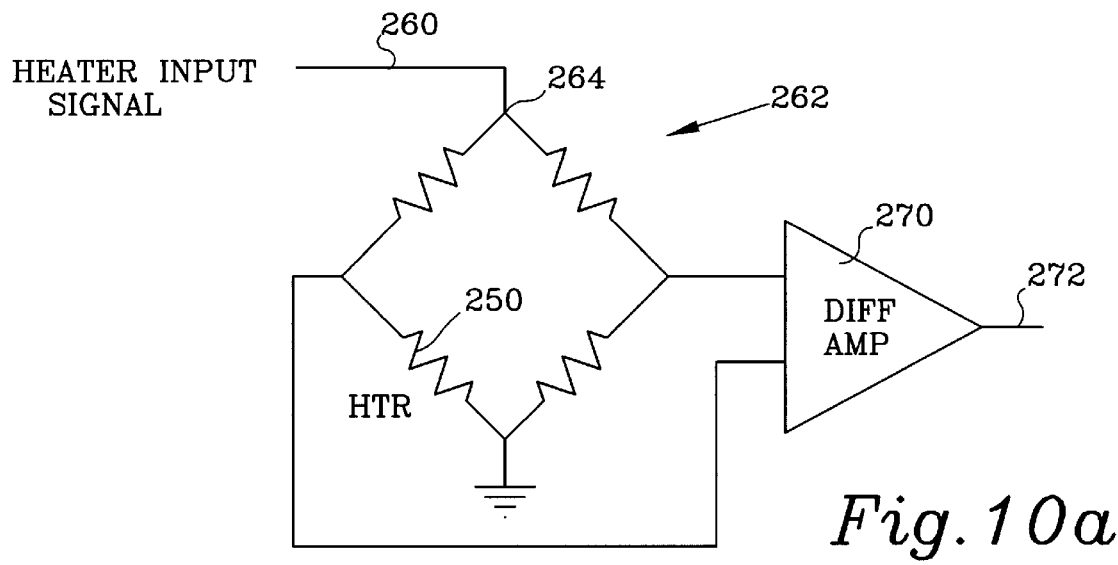
FIG. 10 is a schematic diagram of an illustrative circuit for use with the microbridge heater and sensor elements of FIG. 7.
Figure 10B:
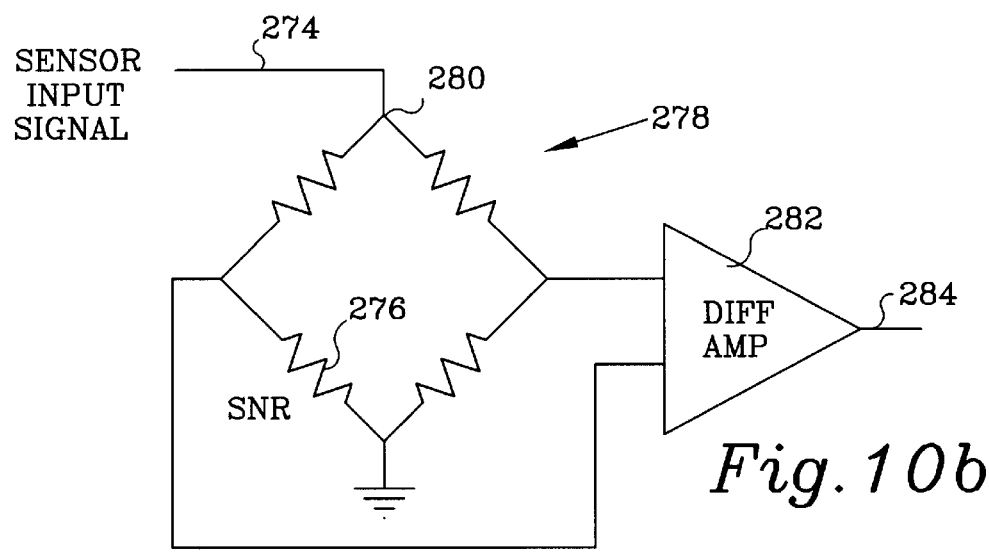

FIG. 10 is a schematic diagram of an illustrative circuit for use with the microbridge heater and sensor elements of FIG. 7. In accordance with the present invention, a periodic time-varying heater input signal 260 is provided to a heater element 250. The heater element 250 is disposed in and closely coupled to a fluid medium (gas or liquid) of interest. To simultaneously provide power to, and measure the resistance response of the heater element 250, the heater element 250 may be incorporated into one leg of a Wheatstone bridge 262, as shown. The time varying heater input signal 260 is provided to a power input terminal 264 of the Wheatstone bridge 262, which is either directly or indirectly coupled to the heater element 250. In this configuration, the Wheatstone bridge 262 provides a differential output signal that has an amplitude that is proportional to the resistance of the heater element 250. Preferably, the differential output signal is provided to a differential amplifier circuit 270 to provide an amplified output signal 272.

The heater input signal 260 provides power to the heater element 250 and induces a transient elevated temperature condition in the heater element 250 and the fluid of interest. Because the heater element 250 is closely coupled to the fluid, the thermal conductivity, k, of the fluid directly affects the time variable temperature response of the heater element 250. Further, the thermal conductivity of the fluid is typically dependent on the pressure and/or temperature of the fluid. Thus, it has been found that the thermal conductivity, pressure and/or temperature of the fluid of interest can be determined by examining a variable phase lag or time lag between the input signal 260 provided to the heater element 250 and a subsequent transient temperature response of the heater element 250.

Likewise, a periodic time-varying sensor input signal 274 may be provided to a sensor element 276. The sensor element 276 is spaced from the heater element and disposed in and closely coupled to a fluid medium (gas or liquid) of interest. To simultaneously provide power to, and measure the resistance response of the sensor element 276, the sensor element 276 may be incorporated into one leg of a Wheatstone bridge 278, as discussed above. The sensor input signal 274 is provided to a power input terminal 280 of the Wheatstone bridge 278, which is either directly or indirectly coupled to the sensor element 276 as shown. In this configuration, the Wheatstone bridge 278 provides a differential output signal that has an amplitude that is proportional to the resistance of the sensor element 276. Preferably, the differential output signal is provided to a differential amplifier circuit 282 to provide an amplified output signal 284.

Using the circuit shown in FIG. 10, the heater time lag $\Delta z_h$ and the sensor time lag $\Delta z_s$ can be determined by monitoring the transient temperature responses of the heater and sensor elements, respectively. To obtain a more accurate transit time $\Delta z_t$ for the temperature disturbance in the fluid during operation, the heater time lag $\Delta z_h$ and the sensor time lag $\Delta z_s$ may be subtracted from the time lag measured between the heater input signal and the resulting temperature response of the sensor element.

Moreover, the circuit shown in FIG. 10 may be used to introduce heat into the sensor element via the sensor input signal 274. The sensor input signal 274 is preferably controlled to provide a frequency, phase and amplitude that produce a resulting temperature response in the sensor element 276 that tracks the temperature disturbance of the fluid. When this condition is satisfied, substantially zero heat is transferred from the fluid to the sensor element 276.

Figure 11:
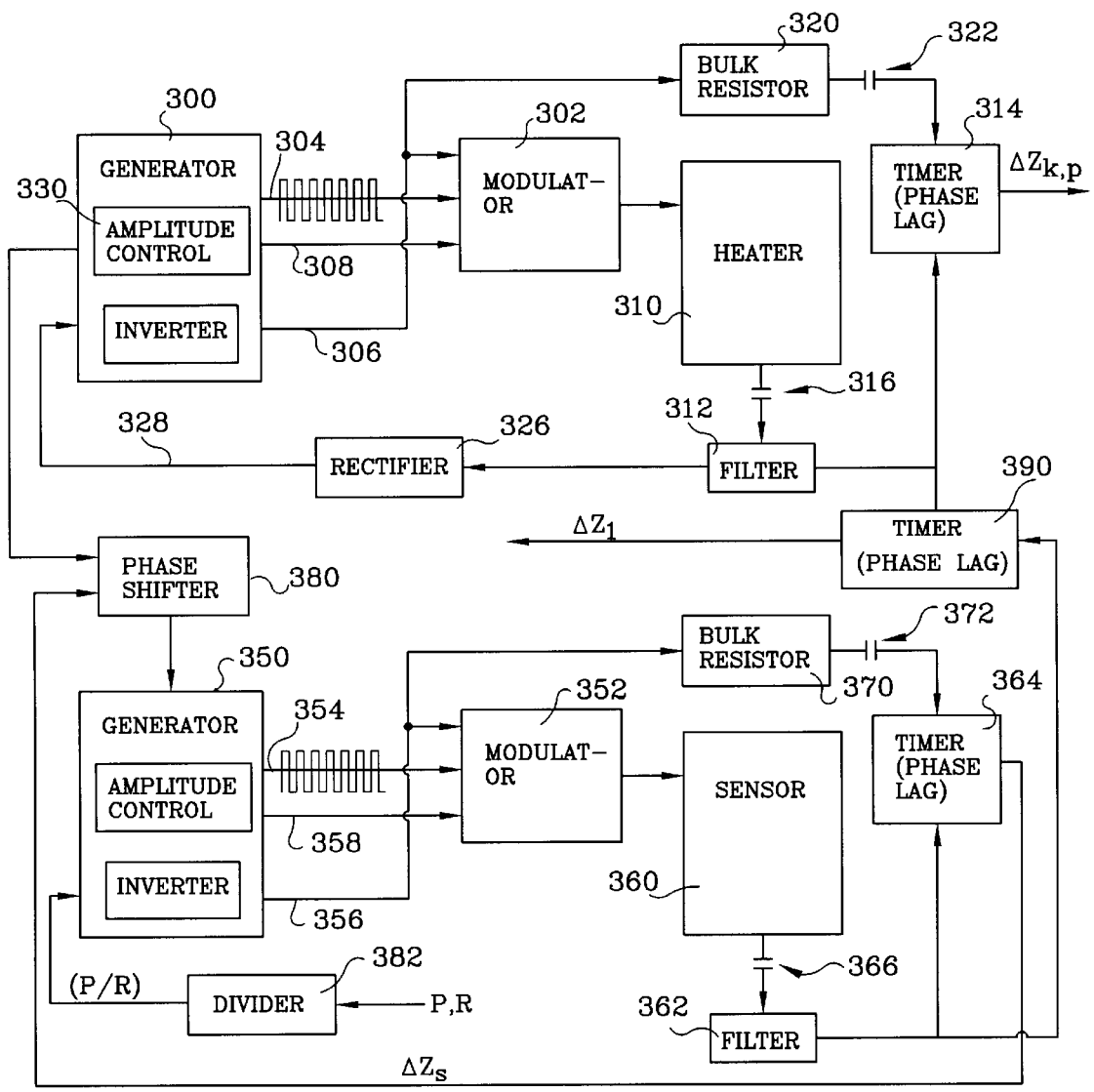
FIG. 11 is a block diagram showing another illustrative embodiment of the present invention for obtaining various time lags values used to determine the thermal conductivity, thermal diffusivity, and specific heat of the fluid of interest.

FIG. 11 is a block diagram showing another illustrative embodiment of the present invention for obtaining various time lags values to determine the thermal conductivity, thermal diffusivity, and specific heat of the fluid of interest. In this embodiment, heat is introduced into the sensor element via a sensor input signal during operation. The sensor input signal is carefully controlled to provide a frequency, phase and amplitude that produce a resulting temperature response in the sensor element that tracks the temperature disturbance of the fluid.

In this illustrative embodiment, the heater input signal and the sensor input signal include both a high frequency component and a lower frequency component. The lower frequency component preferably modulates the high frequency component. This construction allows an accurate dosage of power to be delivered to the heater element, while eliminating frequency doubling effects that may occur without adding a DC component to the input signal. The high frequency component is preferably in the range of 0.1 to 3 MHz, while the lower frequency component is preferably in the range of 30 to 200 Hz.

Figure 13:
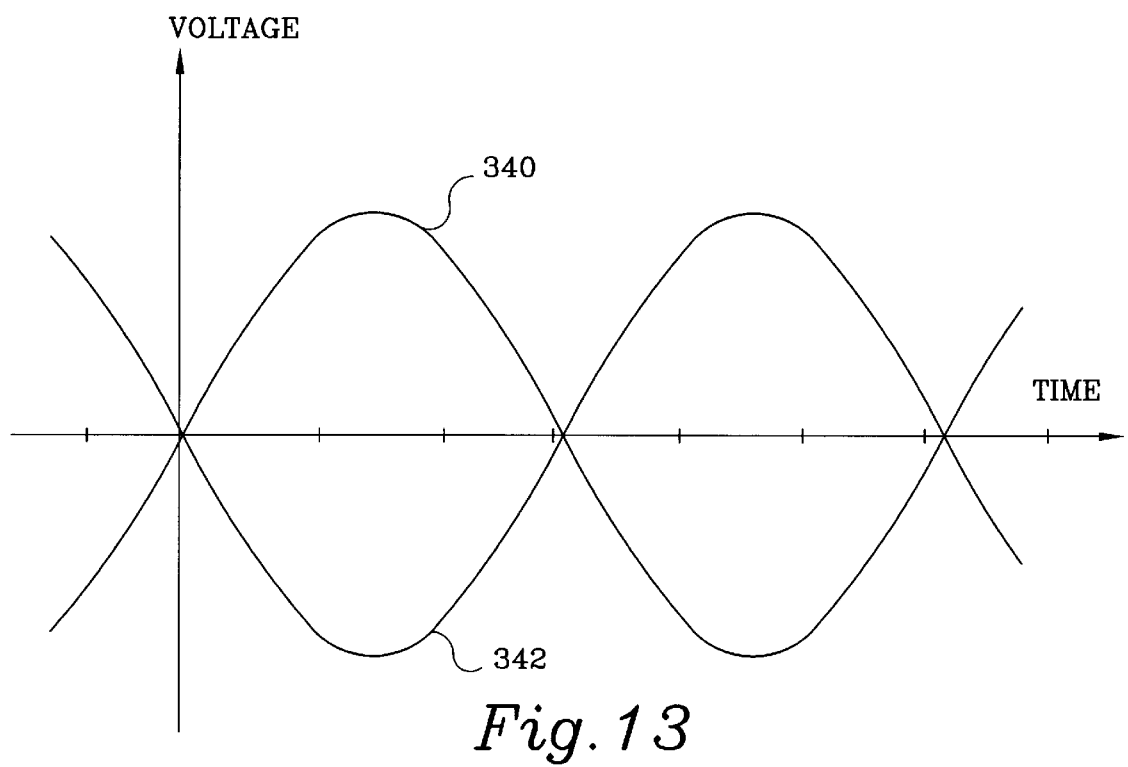
FIG. 13 is a timing diagram showing an illustrative input signal, and an inverted copy thereof, which are provided by the signal generators shown in FIG. 11.
Figure 14:
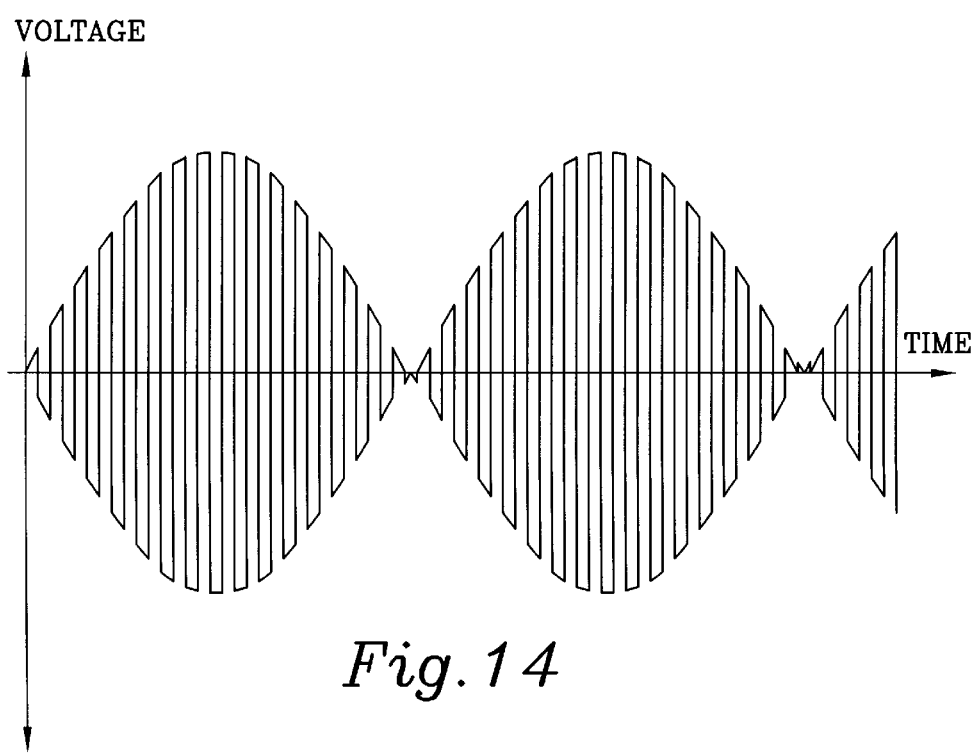
FIG. 14 is a timing diagram showing an illustrative high frequency signal modulated by the input signals of FIG. 13.
Figure 15:
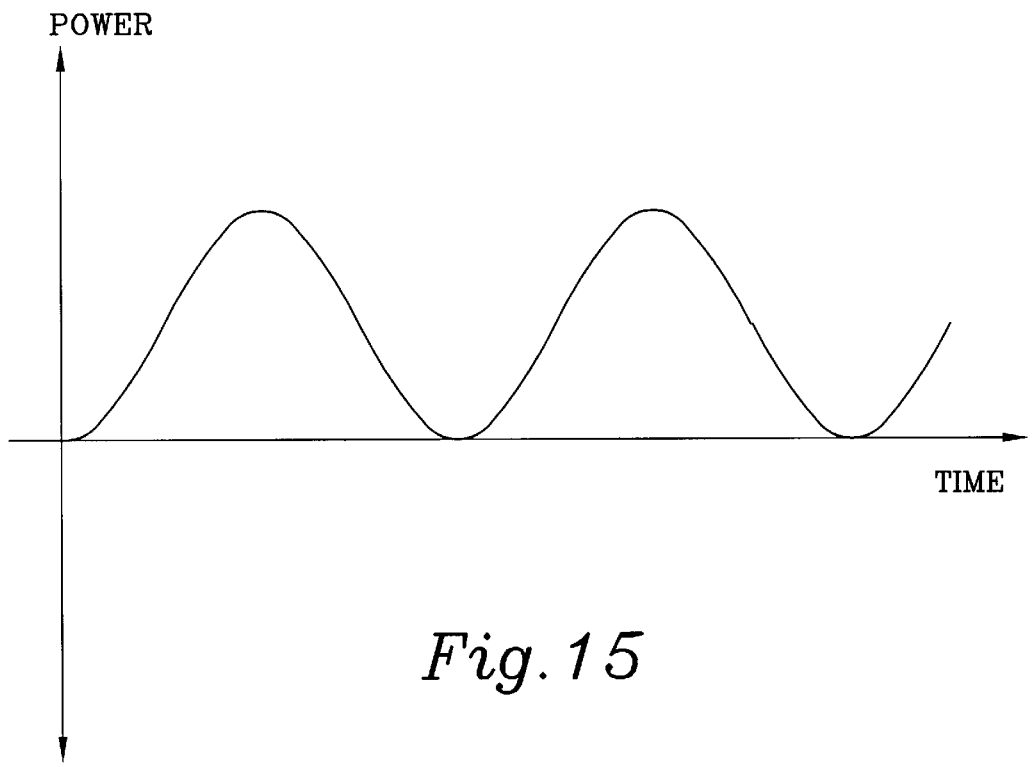
FIG. 15 is a timing diagram showing the power of the modulated input signal of FIG. 14.

With respect to the heater element, a first generator 300 generates and provides the high frequency component of the input signal to a modulator 302 via interface 304. The generator 300 also generates the lower frequency component, and an inverted copy thereof, and provides these signals to modulator 302 via interfaces 306 and 308, respectively. An illustrative lower frequency component 340 and inverted copy thereof 342 are shown in FIG. 13. The modulator 302 modulates the high frequency component using the lower frequency component signals to produce a modulated heater input signal. An illustrative modulated heater input signal is shown in FIG. 14. The power delivered by the modulated heater input signal is shown in FIG. 15.

The modulated heater input signal is provided to heater block 310. To simultaneously provide power to, and measure the resistance response of the heater element, the heater element is preferably provided in one leg of a Wheatstone bridge, for example as shown in FIG. 10. Thus, in the illustrative embodiment, the heater block 310 preferably includes a circuit similar to that shown in FIG. 10.

Figure 16:
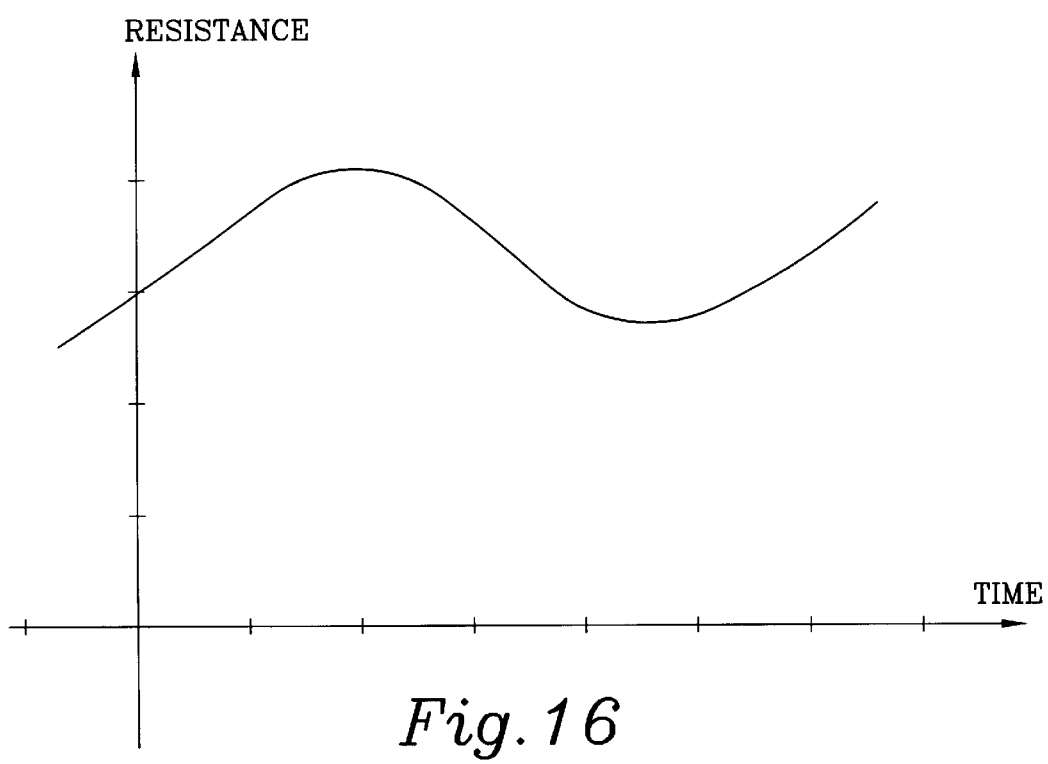
FIG. 16 is a timing diagram showing the resistance of the heater and/or sensor elements versus time when the power signal of FIG. 15 is provided thereto.

The modulated heater input signal is provided to a power input terminal of the Wheatstone bridge, such as power input terminal 264 of FIG. 10, which is either directly or indirectly coupled to the heater element. In this configuration, the Wheatstone bridge provides a differential output signal with an amplitude that is proportional to the resistance of the heater element. The differential output of the Wheatstone bridge may be provided to a differential amplifier, as shown in FIG. 10, or may be directly provided as the output of heater block 310. An illustrative transient resistance response of the heater element is shown in FIG. 16.

For accurate measurement of the heater resistance, the high frequency component may be removed from the heater output signal of the Wheatstone bridge using any number of techniques. One such technique is to provide a low-pass filter 312 at the output of the heater block 310 which allows only the lower frequency component of the heater output signal to pass. The resulting filtered signal may then be provided to a stop input of a first high frequency timer 314. Preferably, the heater output signal of the heater block 310 is AC coupled to the filter 312, as shown by capacitor 316. The filter 312 may provide the AC coupling function, or a separate element such as capacitor 316 may be provided.

The start input of the first high frequency timer 314 may be coupled to the lower frequency component of the heater input signal. More preferably, however, the lower frequency component of the heater input signal is coupled to the start input of the high frequency timer 314 via a bulk resistor 320 and a capacitor 322 as shown. In any case the start input of the high frequency timer 314 is responsive to the lower frequency component of the heater input signal. The bulk resistor 320 preferably has a low temperature coefficient to minimize any phase lag caused thereby. Capacitor 322 AC couples the lower frequency component of the input signal to the start input of the high frequency timer 314.

Because both the heater input signal and the heater output signal are preferably AC coupled to the timer start and stop inputs, respectively, of the timer 314, the zero crossing points of the heater input and output signals may be used to trigger the high frequency timer 314. This allows the time lag measurement of the high frequency timer 314 to be relatively independent of the amplitudes of the input and output signals, thereby increasing the accuracy of the measurement.

As can be seen from the above description, high frequency timer 314 starts when the AC coupled lower frequency component of the heater input signal crosses some predefined threshold, preferably zero. Likewise, high frequency timer 314 stops when the AC coupled heater output signal, which represents the resistance of the heater element, crosses some predefined threshold, preferably zero. The result is a heater time lag $\Delta z_h$ (a.k.a $\Delta z_{k,p}$).

In some applications, it may be desirable to control the amplitude of the transient elevated temperature condition of the heater element. This is preferably accomplished by providing an amplitude control signal that is indicative of the amplitude of the resistance change in the heater element. The amplitude control signal may be provided by a rectifier 326, which rectifies the filtered output signal as shown. The generator 300 may include an amplitude control block 330, which accept the amplitude control signal via interface 328, and adjusts the amplitude of the lower frequency component and the inverted copy thereof such that the amplitude of the resistance change in the heater element remains at a relatively constant level.

With respect to the sensor element, a second generator 350 generates and provides the high frequency component of the sensor input signal to a modulator 352 via interface 354. The generator 350 also generates the lower frequency component, and an inverted copy thereof, and provides these signals to modulator 352 via interfaces 356 and 358, respectively. As described above, the modulator 352 modulates the high frequency component using the lower frequency component signals to produce a modulated sensor input signal as shown in FIG. 14. The power delivered by the modulated sensor input signal is shown in FIG. 15.

The modulated sensor input signal is provided to sensor block 360. To simultaneously provide power to, and measure the resistance response of the sensor element, the sensor element is preferably provided in one leg of a Wheatstone bridge, for example as shown in FIG. 10. Thus, in the illustrative embodiment, the sensor block 360 preferably includes a circuit similar to that shown in FIG. 10.

The modulated sensor input signal is provided to a power input terminal of the Wheatstone bridge, such as power input terminal 280 of FIG. 10, which is either directly or indirectly coupled to the sensor element. In this configuration, the Wheatstone bridge provides a differential output signal with an amplitude that is proportional to the resistance of the sensor element. The differential output of the Wheatstone bridge may be provided to a differential amplifier, as shown in FIG. 10, or may be directly provided as the output of sensor block 360. An illustrative transient resistance response of the sensor element is shown in FIG. 16.

For accurate measurement of the sensor resistance, the high frequency component of the modulated heater input signal may be removed using any number of techniques. One such technique is to provide a low-pass filter 362 at the output of the sensor block 360 which only allows the lower frequency component of the sensor output signal to pass. The resulting filtered signal may then be provided to a stop input of a second high frequency timer 364. Preferably, the sensor output signal of the sensor block 360 is AC coupled to the filter 362, as shown by capacitor 366. The filter 362 may provide the AC coupling function, or a separate element such as capacitor 366 may be provided.

The start input of the second high frequency timer 364 may be coupled to the lower frequency component of the sensor input signal. More preferably, however, the lower frequency component of the heater input signal is coupled to the start input of the second high frequency timer 364 via a bulk resistor 370 and a capacitor 372 as shown. The bulk resistor 370 preferably has a low temperature coefficient to minimize any phase lag caused thereby. Capacitor 372 AC couples the lower frequency component of the sensor input signal to the start input of the high frequency timer 364.

Because both the sensor input signal and the sensor output signal are AC coupled to the timer start and stop inputs, respectively, of the timer 364, the zero crossing points of the sensor input and output signals may be used to trigger the high frequency timer 364. This allows the time lag measurement of the second high frequency timer 364 to be relatively independent of the amplitudes of the sensor input and output signals, thereby increasing the accuracy of the measurement.

As can be seen from the above description, high frequency timer 364 starts when the AC coupled lower frequency component of the sensor input signal crosses some predefined threshold, preferably zero. Likewise, high frequency timer 364 stops when the AC coupled heater output signal, which represents the resistance of the sensor element, crosses some predefined threshold, preferably zero. The result is a sensor time lag $\Delta z_s$.

Figure 17:
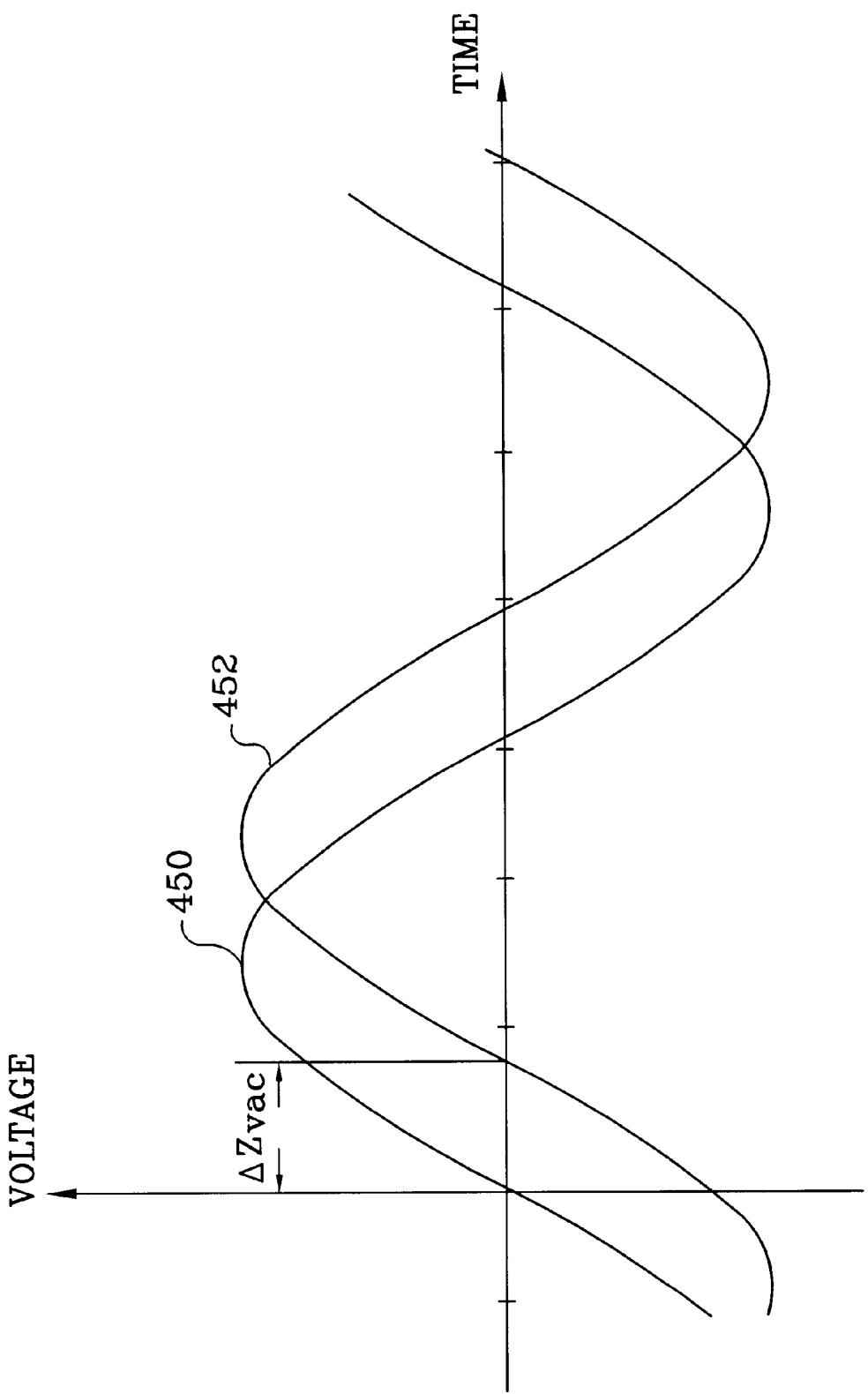
FIG. 17 is a timing diagram showing the sensor time lag $\Delta z_{svac}$ when measured under vacuum conditions.

To provide a sensor input signal that has the proper frequency, phase and amplitude to cause the resulting temperature response in the sensor element to track the temperature disturbance of the fluid, a phase shifter 380 and analog divider 382 are provided. The desired phase and amplitude of the sensor input signal can be determined during a calibration procedure. In a preferred embodiment, the sensor element is first subjected to a vacuum condition, and a sensor input signal is provided to the sensor element as described above. Because no fluid surrounds the sensor element, substantially no heat is transferred from the sensor element to the fluid. A sensor time lag $\Delta z_{svac}$ is measured by the high frequency timer 364, and subsequently stored. The sensor time lag $\Delta z_{svac}$ is shown in FIG. 17 as the delay between the sensor input signal 450 and the resistive response 452 of the sensor element. In addition, a power/resistance ratio between the sensor input signal and the resulting resistance response of the sensor element is measured and stored.

The sensor element is then subjected to a fluid of interest. During operation, the phase of the sensor input signal is adjusted by phase shifter 380 so that the resulting sensor time lag $\Delta z_s$, measured by high frequency timer 364, equals the sensor time lag measured under vacuum conditions $\Delta z_{svac}$. Generator 350 may include a comparator for comparing the measured time lag $\Delta z_s$ and the calibrated time lag $\Delta z_{svac}$.

Likewise, the power of the input signal (P) and the resulting resistance response (R) of the sensor element may be provided to analog divider 382, as shown. Analog divider 382 may divide these signals to provide a power/resistance ratio. Generator 350 may then adjust the amplitude of the sensor input signal so that the resulting power/resistance ratio equals the power/resistance ratio recorded under vacuum conditions.

Accordingly, the sensor input signal heats the sensor element in phase and with the proper amplitude to match the temperature disturbance in the fluid such that substantially no heat is transferred from the fluid to the sensor element. This may help reduce or eliminate the sensor time lag $\Delta z_s$ as a factor when determining the transit time of the temperature disturbance.

Timer 390 directly measures the transit time $\Delta z_1$ of the temperature disturbance from the heater element to the sensor element. Timer 390 is started when the response of the heater element crosses a predefined threshold, preferably zero. Timer 390 is stopped with the response of the sensor element crosses a predefined threshold, preferably zero. Since the sensor is tracking the temperature disturbance in the fluid, the sensor time lag $\Delta z_s$ is negligible. Thus, the thermal diffusivity and specific heat of the fluid of interest can be calculated using the transit time $\Delta z_1$, and the thermal conductivity, k, of the fluid of interest.

Figure 12:
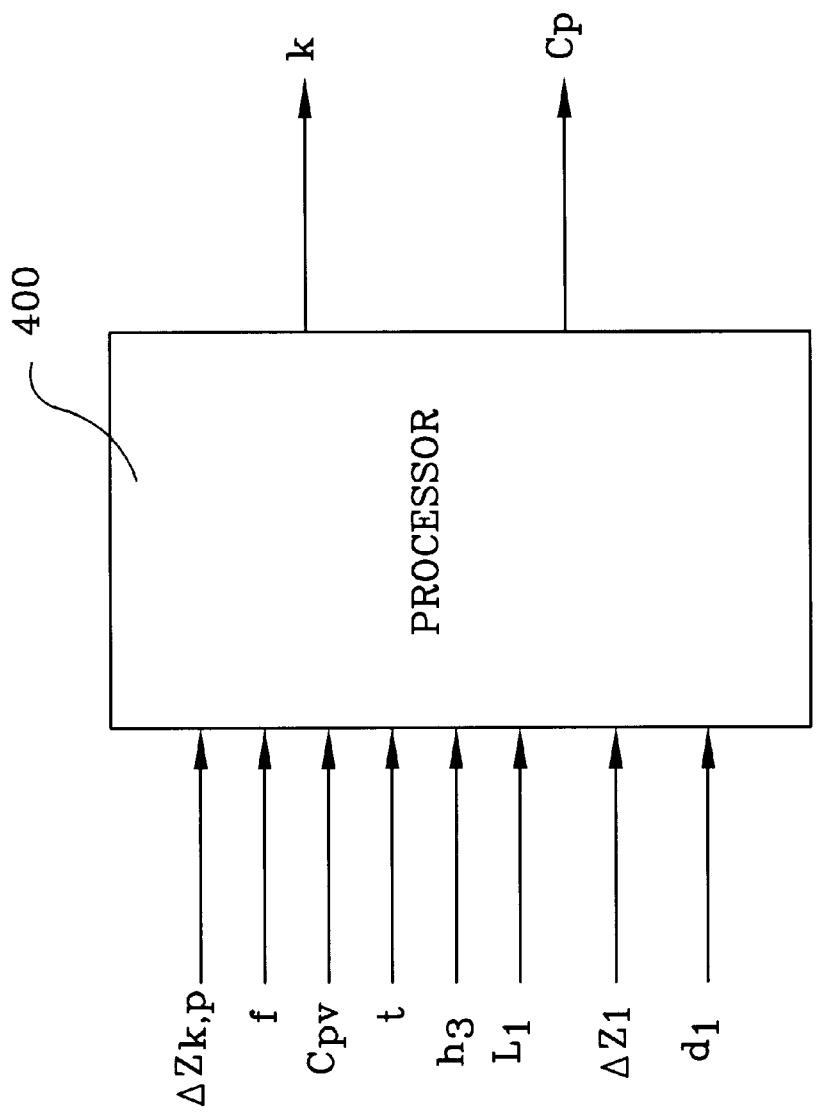
FIG. 12 is a block diagram showing a processing means that is used for calculating the thermal conductivity and specific heat of the fluid of interest using the time lag values provided by FIG. 11.

FIG. 12 is a block diagram showing a processing means 400 that is used to calculate the thermal conductivity, thermal diffusivity, and specific heat of the fluid of interest using the time lag values provided by FIG. 11. Before providing the relations for determining the thermal conductivity, thermal diffusivity and specific heat of a fluid of interest from the time lag values $\Delta z_{k,p}$ and $\Delta z_1$, some background information may be helpful.

THERMAL CONDUCTIVITY

The thermal dynamic interaction between a heater element that is forced to experience fluctuating temperatures of:

$$T = T_0 + T_1 \sin(\omega z + \gamma) \quad (1)$$

in response to a fluctuating input power $$P = P_0(1 + \sin(\omega z)) \quad (2)$$

can be described by a simple differential equation $$C_{pv} t \, dT/dz = P_0(1 + \sin(\omega z)) - (h_1 + h_2)(T - T_f) - h_3(T - T_b) \quad (3)$$

Reference to the table of symbols below may be helpful to the understanding of these equations.

TABLE I

| Symbol | Nomenclature |
|---|---|
| f | frequency of the input signal, $H_z$ |
| $\omega$ | $2\pi f$, $H_z$ |
| $c_{pv}$ | specific heat per unit volume for the heater film and support member (10% Platinum, 90% $Si_3N_4$ Microbridge composite, $J/(cm^3 k)$) |
| t | heater film thickness, cm |
| T | sensor base temperature, with peak-to-peak amplitude of $2T_0$, k |
| $T_f$ | fluid temperature, k |
| $T_b$ | substrate temperature, k |
| $h_1$ | coefficient of conductive heat transfer to the fluid of interest ($= k/L_1$), $W/cm^3$ |
| $h_2$ | coefficient of forced convective heat transfer to the fluid of interest under laminar flow ($= k/L_2$), $W/cm^3$ |
| $h_3$ | coefficient of conductive heat transfer to the substrate, $W/cm^3$ |
| $L_1$ | characteristic length of thermal conduction from the heater element into the fluid phase, cm |
| $L_2$ | characteristic length of convective heat transfer, cm |
| z | time, s |
| T | Temperature |
| $\Delta z_h$ | time lag between the heater input signal and the resistance response of the heater means |
| $\Delta z_s$ | time lag between the sensor input signal and the resistance response of the sensor means |
| $\Delta z_{svac}$ | time lag between the sensor input signal and the resistance response of the sensor means under vacuum conditions |
| $\Delta z_1$ | time lag between the heater response and the sensor response, with $\Delta z_s = \Delta z_{svac}$ |
| $d_1$ | separation distance between the heater element and the sensor element |
| $\gamma$ | phase lag between input signal and the resistance of the heater means ($\gamma = \Delta z \cdot 2\pi f$), radians |

Integration of equation (3) leads to the solution for the phase lag, $\gamma$, and the DC and AC signal amplitudes, $T_0$ and $T_1$, respectively as follows:

$$\gamma = \arctan(-2\pi f c_{pv} t/(h_1 + h_2 + h_3)) \quad (4)$$

$$\Delta z = -\gamma/(2\pi f) \quad (5)$$

$$T_0 = ((h_1 + h_2)T_f + h_3 T_b + P_0)/(h_1 + h_2 + h_3) \quad (6)$$

$$T_1 = P_0/((h_1 + h_2 + h_3)^2 + (c_{pv} t\omega)^2)^{1/2} \quad (7)$$

The contributions of $h_1$, $h_2$ and $h_3$ to the phase lag $\gamma$ can be isolated and individually measured. During a calibration procedure, for example, the value of $h_3$ can be determined by subjecting the heater element to a vacuum condition, thereby reducing $h_1$ and $h_2$ to zero. A time lag value may then be measured between the input signal and the output signal of the heater element under the vacuum condition. The value of $h_2$ may then be calculated using the relation:

$$h_3 = -2\pi f c_{pv} t/\tan(\gamma) \quad (8)$$

The value of $h_1$ may then be determined by subjecting the heater element to the fluid of interest at atmospheric pressure and substantially zero flow, thereby reducing $h_2$ to zero. A time lag can then be measured between the input signal and the output signal of the heater element under atmospheric pressure. The value of $h_1$ can then be calculated using the relation:

$$h_1 = [-2\pi f c_{pv} t/\tan(\gamma)] - h_3 \quad (9)$$

where $h_3$ is known from equation (8).

Finally, the value of $h_2$ may be determined by subjecting the heater means to the fluid of interest at a predetermined non-zero flow rate. A time lag can then be measured between the input signal and the output signal of the heater means under the non-zero flow condition. The value of $h_2$ can then be calculated using the relation:

$$h_2[-2\pi f c_{pv} t/\tan(\gamma)] - h_1 - h_3 \qquad (10)$$

where $h_2$ and $h_3$ are known from equations (8) and (9).

In the illustrative embodiment shown in FIG. 7, the heater element 250 and the support member 252 have a composite specific heat value, $c_{pv}$. Further, the heater element 250 has a coefficient of conductive heat transfer to the substrate 254, $h_3$. Once these parameters are determined, for example by prior calibration as described above, the thermal conductivity, k, of the fluid of interest can be determined at substantially zero flow, after determining L, via a fluid of known k, by using the relation:

$$k = (-2\pi f c_{pv} t/\tan(\gamma) - h_3) L_1 \qquad (11)$$

THERMAL DIFFUSIVITY AND SPECIFIC HEAT

The propagation or spread of a local, non-uniform temperature distribution can be derived from the following three-dimensional temperature diffusivity or heat conductivity equation, to which a term has been added to represent fluid velocity in the x-direction:

$$\delta T/dz = D_t \Delta d^2 T/dx^2 - v_x dT/dx \qquad (12)$$

The one dimensional transient solution to equation (12) is:

$$T - z^{0.5} \exp(-(d_1 - vz)^2/(4D_t z)) \qquad (13)$$

where x has been replaced by $(\pm d1 \pm vz)$ to include the velocity term. To determine the time lag between very short forcing functions at time z=0 and the arrival of these pulses in terms of maxima in T(z) at the sensor element position $d_1$, dT/dz is set equal to zero. Differentiating equation (13) and setting the result equal to zero yields:

$$dT/dz = 0 = -1/z^2 + (1/z)(2v(d_1 - vz)/4D_t z + (d_1 - vz)^2/4D_t z^2) \qquad (14)$$

multiplying by $Z^2$ and rearranging yields the relation:

$$-4D_t z - v^2 z^2 + d_1^2 = 0 \qquad (15)$$

Because the present invention contemplates determining the thermal conductivity, thermal diffusivity and specific heat of the fluid of interest at substantially zero flow, v is set to zero, resulting in the following relation for $D_t$:

$$D_t = d_1^2/(4\Delta z_1) \qquad (16)$$

where z has been replaced by $\Delta z_1$, which represents the transit time for the temperature disturbance to travel a distance d1, or in this case, from the heater element to the sensor element. This relation may be used by the processing means 400 to determine the thermal diffusivity of the fluid of interest.

The processing means 400 may also calculate the specific heat of the fluid of interest by using the relation:

$$c_p = k/D_t \qquad (17)$$

where the thermal conductivity, k, and the thermal diffusivity, $D_t$, are determined as described above.

FIG. 18 is a timing diagram showing the various time lags measured by the embodiment of FIG. 11. The heater time lag value $\Delta z_{k,p}$ is determined as described above, and represents the time lag between the heater input signal shown at 500 and the response of the heater element shown at 502. As described above, the heater time lag $\Delta z_{k,p}$ is preferably used to calculate the thermal conductivity of the fluid of interest.

In the embodiment shown and described with reference to FIG. 11, the sensor time lag $\Delta z_s$ is forced to match the sensor time lag under vacuum conditions $\Delta z_{svac}$. Thus, the sensor input signal shown at 506 is provided with the proper phase relative to the heater input signal, and with the proper amplitude, so that the substantially no heat is transferred from the fluid to the sensor element. The temperature response of the sensor element is shown at 508.

The transit time $\Delta z_1$ is the time lag between the heater response and the sensor response, with $\Delta z_s = \Delta z_{svac}$ as shown. As described above, the transit time $\Delta z_1$ is preferably used to calculate the thermal diffusivity and the specific heat of the fluid of interest.

Having thus described the preferred embodiments of the present invention, those of skill in the art will readily appreciate that the teachings found herein may be applied to yet other embodiments within the scope of the claims hereto attached.

What is claimed is:

1. Apparatus for determining a selected property of a fluid of interest, comprising:

heater means in thermal communication with the fluid of interest, said heater means having a resistance that changes with temperature;

heater energizing means connected to said heater means for energizing said heater means, said heater energizing means providing a transient elevated temperature condition in said heater means;

sensor means in thermal communication with the fluid of interest and spaced from said heater means, said sensor means having a resistance that changes with temperature;

first time lag means for determining a first time lag between the transient elevated temperature condition of said heater means and a transient elevated temperature response of said sensor means; and determining means for determining the selected property of the fluid of interest using the first time lag.

2. Apparatus according to claim 1 further comprising sensor energizing means for energizing said sensor means with an input power signal that has a phase relative to the periodic time-varying input signal of said heater energizing means such that substantially no heat is transferred from the fluid of interest to the sensor means during the transient elevated temperature condition.

3. Apparatus according to claim 1 wherein said determining means determines the thermal diffusivity $D_t$ of the fluid of interest based on the relation:

$$D_t = d^2/4\Delta z$$

where, d = the separation distance between said heater means and said sensor means, $\Delta z$ = the first time lag between the transient elevated temperature condition of said heater means and said transient elevated temperature condition of said sensor means as determined by said first time lag means.

4. Apparatus according to claim 3 further comprising means for determining the specific heat $C_p$ of the fluid of interest based on the relation:

$$C_p k/D_t$$

where, k=the thermal conductivity of the fluid of interest, $D_t$=the thermal diffusivity $D_t$ determined in claim 3.

5. Apparatus according to claim 1 wherein said heater energizing means provides a periodic time-varying input signal to said heater means to induce a transient elevated temperature condition in said heater means, said apparatus further comprising first output means for providing a first output signal that is proportional to the resistance of said heater means.

6. Apparatus according to claim 5 further comprising sensor energizing means for energizing said sensor means, said sensor energizing means providing a periodic time-varying input signal to said sensor means that is shifted in phase relative to the periodic time-varying input signal of said heater energizing means.

7. Apparatus according claim 6 further comprising:

second output means for providing a second output signal that is proportional to the resistance of said sensor means; and second time lag means for determining a second time lag between the input power signal provided by said sensor energizing means and the second output signal.

8. Apparatus according to claim 7 wherein said sensor energizing means comprises a phase shifter for shifting the phase of the periodic time-varying input signal provided by said heater energizing means by an amount which causes said second time lag to be substantially equivalent to a predetermined value.

9. Apparatus according to claim 8 wherein said predetermined value is equivalent to the second time lag when measured with said sensor means under a vacuum condition.

10. Apparatus according to claim 9 wherein the input power signal provided by said sensor energizing means has an amplitude, wherein said amplitude is selected to provide a power-resistance ratio in said sensor means that is substantially identical to the power-resistance ratio in said sensor means when measured under a vacuum condition.

11. Apparatus for determining selected characteristics of a fluid of interest, comprising:

heater means in thermal communication with the fluid of interest, said heater means having a resistance that changes with temperature;

heater energizing means connected to said heater means for energizing said heater means, said heater energizing means providing a periodic time-varying input signal to said heater means to induce a transient elevated temperature condition in said heater means;

sensor means in communication with the fluid of interest and spaced from said heater means, said sensor means having a resistance that changes with temperature; and sensor energizing means connected to said sensor means for energizing said sensor means, said sensor energizing means providing a periodic time-varying input signal that has a phase relative to said time-varying input signal of said heater energizing means so that substantially no heat is transferred from the fluid of interest to said sensor means during the transient elevated temperature condition.

12. Apparatus according to claim 11 further comprising:

first output means for providing a first output signal that is proportional to the resistance of said heater means;

second output means for providing a second output signal that is proportional to the resistance of said sensor means;

time lag means for determining a time lag between the first output signal and the second output signal during the transient elevated temperature condition; and determining means for determining the thermal diffusivity, $D_t$, of the fluid of interest using the time lag.

13. A method for determining selected characteristics of a fluid of interest under non-vacuum conditions using a heater means and a sensor means, wherein each of said heater means and said sensor means are in thermal communication with the fluid of interest and have a resistance that changes with temperature, the method comprising the steps of:

energizing the heater means with a periodic time-varying input signal to induce a transient elevated temperature condition in said heater means;

energizing the sensor means with a periodic time-varying input signal that has a phase relative to said period time-varying input signal that is provided to the heater means such that substantially no heat is transferred from the fluid of interest to said sensor means during the transient elevated temperature condition.

14. A method according to claim 13 further comprising the calibration steps of:

subjecting the sensor means to a vacuum condition;

applying a calibration time-varying input signal to the sensor means to provide a transient elevated temperature condition in the sensor means; and measuring a vacuum time lag between the calibration time-varying input signal and the resulting elevated temperature response in the sensor means.

15. A method according to claim 14 further comprising the steps of:

subjecting the heater means and the sensor means to the fluid of interest;

measuring the time lag between the time-varying input signal to the sensor means and the corresponding transient elevated temperature response in the sensor means; and shifting the periodic time-varying input signal that is provided to the sensor means by a sufficient amount to cause the measured time lag to substantially match the vacuum time lag.

16. A method according to claim 14 further comprising the calibration steps of:

measuring a power-resistance ratio between the power of the input signal to the sensor means and the resulting resistance of the sensor means during the elevated temperature condition under vacuum conditions.

17. A method according to claim 14 further comprising the steps of:

subjecting the heater means and the sensor means to the fluid of interest;

measuring the time lag between the time-varying input signal to the sensor means and the corresponding transient elevated temperature response in the sensor means;

shifting the periodic time-varying input signal that is provided to the sensor means by a sufficient amount to cause the measured time lag to substantially match the vacuum time lag;

measuring a power-resistance ratio between the power of the input signal to the sensor means and the resistance of the sensor means during the elevated temperature condition; and modifying the amplitude of the periodic time-varying input signal that is provided the sensor means by a sufficient amount to cause the measured power-resistance ratio to substantially match a predetermined vacuum power-resistance ratio.

* * * * *